United States Patent
Nguyen et al.

(10) Patent No.: US 11,363,958 B2
(45) Date of Patent: Jun. 21, 2022

(54) SYSTEMS, ARTICLES AND METHODS FOR CARDIOLOGY SENSORY TECHNOLOGY

(71) Applicant: HelpWear Inc., Toronto (CA)

(72) Inventors: Frank Nguyen, North York (CA); Andre David Thomas Bertram, Toronto (CA)

(73) Assignee: HelpWear Inc., Toronto (CA)

( * ) Notice: Subject to any disclaimer, the term of this patent is extended or adjusted under 35 U.S.C. 154(b) by 89 days.

(21) Appl. No.: 16/496,139

(22) PCT Filed: Mar. 23, 2018

(86) PCT No.: PCT/CA2018/050359
§ 371 (c)(1),
(2) Date: Sep. 20, 2019

(87) PCT Pub. No.: WO2018/170607
PCT Pub. Date: Sep. 27, 2018

(65) Prior Publication Data
US 2020/0029840 A1     Jan. 30, 2020

Related U.S. Application Data

(60) Provisional application No. 62/475,589, filed on Mar. 23, 2017.

(51) Int. Cl.
*A61B 5/024* (2006.01)
*G16H 80/00* (2018.01)
(Continued)

(52) U.S. Cl.
CPC .......... *A61B 5/02438* (2013.01); *A61B 5/333* (2021.01); *A61B 5/364* (2021.01); *G16H 80/00* (2018.01)

(58) Field of Classification Search
None
See application file for complete search history.

(56) References Cited

U.S. PATENT DOCUMENTS

2007/0273504 A1    11/2007  Tran
2010/0204595 A1*   8/2010   Marx .................. A61B 5/6831
                                                                600/509
(Continued)

FOREIGN PATENT DOCUMENTS

CA          3021919         9/2018

OTHER PUBLICATIONS

International Search Report & Written Opinion dated Jul. 3, 2018 for PCT/CA2018/050359.
(Continued)

*Primary Examiner* — Erica S Lee

(57) ABSTRACT

Device and methods for a wearable medical device are disclosed. The device and methods use an on-board mobile system to alert emergency services when the user is in cardiovascular distress. The device takes advantage of newly miniaturized electrocardiograph, pulse oximetry sensors, mutual reinforcement and anomaly detection algorithms. Electrocardiograph waveforms are recorded digitally for physician review with emphasis on critical events. In the occurrence of a immediate critical-need cardiac event, the system will contact emergency services (EMS) for assistance. The system is a biometric monitoring system that implements key concepts of cardiovascular monitoring through pulse oximetry and electrocardiography (ECG). The system implements key concepts of ECGs and active/capacitive electrodes to produce a wireless network of (individually isolated) ECG nodes that can produce a system ranging from 3 to 16 leads.

22 Claims, 32 Drawing Sheets

(51) Int. Cl.
  *A61B 5/333* (2021.01)
  *A61B 5/364* (2021.01)

(56) References Cited

U.S. PATENT DOCUMENTS

| | | | |
|---|---|---|---|
| 2012/0232369 A1* | 9/2012 | Kim | A61B 5/30 600/372 |
| 2013/0023820 A1* | 1/2013 | Solomon | A61M 5/16827 604/66 |
| 2015/0170503 A1* | 6/2015 | Wedig | G08B 7/06 340/691.5 |
| 2016/0157744 A1* | 6/2016 | Wu | A61B 5/327 600/509 |
| 2016/0302674 A1* | 10/2016 | Moyer | A61B 5/6833 |
| 2016/0310085 A1* | 10/2016 | Delia | A61B 5/6806 |
| 2016/0328529 A1* | 11/2016 | Kaib | A61B 5/366 |
| 2018/0165923 A1* | 6/2018 | Schmit | A61B 5/6843 |
| 2019/0298210 A1* | 10/2019 | Bennet | A61B 5/6833 |

OTHER PUBLICATIONS

Bradycardia (Slow Heart Rate) (n.d.) Retrieved Feb. 25, 2016; from http://www.healthlinkbc.ca/healthtopics/content.asp?hwid=aa107571.
Calculate Your Body Mass (n.d.) Retrieved Feb. 25, 2016; from http://www.nhlbi.nih.gov/health/educational/lose_wt/BMI/bmi-m.htm.
Max Heart Rate before Death Occurs—https://answers.yahoo.com/question/index?qid=20100215135455AAuqIGh&guccounter=1.
Population estimates on Jul. 1, by age and sex; https://www150.statcan.gc.ca/t1/tbl1/en/tv.action?pid=1710000501.
Re: What is the minimum heart rate a concious human can have?; from from http://www.madsci.org/posts/archives/2005-02/1109562000.Me.r.html.
Research Note—Canadian Seniors: A Demographic Profile; http://www.elections.ca/content.aspx?section=res&dir=rec/part/sen&document=index&lang=e.
Impulse response—Wikipedia—https://en.wikipedia.org/wiki/Impulse_response.
Documentation, (n.d.). Retrieved Mar. 11, 2016, from http://www.mathworks.com/help/matlab/ref/fft.html#outputarg_Y.
Measuring Signal Similarities—MATLAB & Simulink Example; http://www.mathworks.com/help/signal/examples/measuring-signal-similarities.html.
Fast Fourier transform—MATLAB fft; http://www.mathworks.com/help/signal/ref/xcorr.html?refresh=true.
Correlation coefficients—MATLAB corrcoef; http://www.mathworks.com/help/matlab/ref/corrcoef.html?refresh=true.
Electrocardiogram (ECG) integrated circuits and reference designs / TI.com; http://www.ti.com/solution/electrocardiogram-ecg.
Elgendi, M. (n.d.). On the Analysis of Fingertip Photoplethysmogram Signals. Retrieved Mar. 11, 2016, from http://www.ncbi.nlm.nih.gov/pmc/articles/PMC3394104/.
Filter Basics: Anti-Aliasing—Tutorial—Maxim https://www.maximintegrated.com/en/app-notes/index.mvp/id/928.
Heart Rate Variability; Standards of Measurement, Physiological Interpretation, and Clinical Use; http://circ.ahajournals.org/doi/full/10.1161/01.cir.93.5.1043.
Heart Rate Variability (HRV) | Polar USA. (n.d.). Retrieved Mar. 9, 2016, from http://support.polar.com/us-en/support/Heart_Rate_Variability_HRV_.
How do I implement cross-correlation to prove two audio files are similar? http://dsp.stackexchange.com/questions/736/how-do-i-implement-cross-correlation-to-prove-two-audio-files-are-similar.
How to measure the similarity between two signal? (n.d.). Retrieved Mar. 7, 2016, from https://www.researchgate.net/post/how_to_measure_the_similarity_between_two_signal.
Matlab Geeks—http://matlabgeeks.com/tips-tutorials/how-to-do-a-fourier-transform-in-matlab.
Mukkamala, R., Hahn, J., Inan, O. T., Mestha, L. K., Kim, C., Toreyin, H., & Kyal, S. (n.d.). Towards Ubiquitous Blood Pressure Monitoring via Pulse Transit Time: Theory and Practice. Retrieved Mar. 5, 2016, from http://www.ncbi.nlm.nih.gov/pmc/articles/PMC4515215/.
Nitzan, M., Patron, A., Glik, Z., & Weiss, A. T. (n.d.). Automatic noninvasive measurement of systolic blood pressure using photoplethysmography. Retrieved Mar. 7, 2016, from http://www.ncbi.nlm.nih.gov/pmc/articles/PMC2772852/.
Plethysmography | Pulse Transit Time (PTT), Pulse Wave Velocity (PWV) and Pulse Wave Amplitude (PWA) | Research | BIOPAC. (n.d.). Retrieved Mar. 11, 2016, from https://www.biopac.com/?app-advanced-feature=pulse-transit-time-ptt-and-relative-bp-measurement.
Pulse Oximeter Pleth (Plethysmograph); https://www.amperordirect.com/pc/help-pulse-oximeter/z-what-is-oximeter-olethysmograph.html.
Removing High-Frequency Noise from an ECG Signal; MATLAB & Simulink; http://www.mathworks.com/help/dsp/ug/removing-high-frequency-noise-from-an-ecg-signal.html.
Techniques for accurate ECG signal processing | EE Times; http7/www.eetimes.com/document.asp?doc_id=1278571.
Techniques for accurate ECG signal processing | EE Times; http://www.eetimes.com/document.asp?doc_id=1278571.
Understanding ECG Filtering; http://www.ems12lead.com/2014/03/10/understanding-ecg-filtering/.
Wireless Brain Signal Recordings based on Capacitive Electrodes; Mehrnaz Kh. Hazrati et al.
Doing FFT in realtime, (n.d.). Retrieved Mar. 11, 2016, from http://stackoverflow.com/questions/6663222/doing-fft-in-realtime.
Electrical Impedance—Wikipedia; https://en.wikipedia.org/wiki/Electrical_impedance.
Cross-correlation—Wikipedia; https://en.wikipedia.org/wiki/Cross-correlation.
Compliance (physiology)—Wikipedia; https://wikipedia.org/wiki/Compliance_(physiology).
Autoregressive model—Wikipedia; https://en.wikipedia.org/wiki/Autoregressive_model.
Pulse wave velocity—Wikipedia; https://en.wikipedia.org/wiki/Pulse_wave_velocity.
Dross-correlation—MATLAB xcorr; https://www.mathworks.com/help/matlab/ref/xcorr.html?refresh=true.
Sensors / Free Full-Text / Dry EEG Electrodes /HTML; https:www.mdpi.com/1424-8220/14/7/12847/htm.
Bio-Sensing—How to measure biological signals and what to do with them; producecosumerobot.com/biosensing/.
Section 12: ECG Artifacts; www.mauvial.com/ECG/ecg_artifact.htm.

* cited by examiner

SYSTEMS, ARTICLES AND METHODS FOR CARDIOLOGY SENSORY TECHNOLOGY

CROSS-REFERENCE TO RELATED APPLICATION(S)

This application is a U.S. nationalization under 35 U.S.C. § 371 of International Application No. PCT/CA2018/050359 filed Mar. 23, 2018 entitled SYSTEMS, ARTICLES AND METHODS FOR CARDIOLOGY SENSORY TECHNOLOGY, which claims the benefit of priority to U.S. Provisional Patent Application No. 62/475,589 filed Mar. 23, 2017 entitled SYSTEMS, ARTICLES AND METHODS FOR CARDIOLOGY SENSORY TECHNOLOGY, all the contents of which are herein incorporated by reference into the below DETAILED DESCRIPTION OF EXAMPLE EMBODIMENTS.

TECHNICAL FIELD

Example embodiments generally relate to wearable sensors and related methods, and more specifically to a wearable heart monitoring and communication system.

BACKGROUND

Heart related illness is a major issue in Canada and all around the world. Over the past decade the number of patients affected by heart related illness has increased by nearly 8% each year. Statistics from The Heart and Stroke Foundation's show that 49% of the Canadian Baby Boomer cohort being at risk of heart failure. The Baby Boomer Cohort now utilizes over $130 billion dollars, or almost 62% of the Canadian healthcare budget annually. This is due to the fact that baby boomers tend to deny that they are at risk. Late response to heart related illness cost $22.2 billion last year in Canada alone, due to costly operating room time, recovery times and treatment plans. Heart related illness has now risen to the point where a Canadian loses their life every 7 minutes. A system is needed that non invasively monitors cardiovascular biometrics around the clock, with real time analysis, which contact emergency services when the user is in distress. This would increase the chances of rapid treatment and avoid costly unnecessary care. The device must seamlessly integrate into the clinical environment for medical professionals to easily operate.

One problem is that emergency room clinicians, family clinicians and even the patients of heart illness have very little to no understanding of their own heart health. This is because available systems are not made for mass use.

There are methods of non-invasive heart monitoring where pulse oximetry is used to determine the user's heart rate. However that is a very baseline analytic method and does not provide a lot of information for the user or for clinicians to act on effectively. The other issue with this method is that data quality will be sacrificed because of movement.

The Holter monitoring systems currently used in hospitals and clinics are inaccessible and are quite expensive, they can only be used on prescription and they only collect data for a short time interval. What this means is that events can be missed because they might not occur in the short time frame.

There are a lot of events that go undiagnosed and this can lead to further issues down the line. Missed cardiac problems can lead to stokes or worse conditions, or even worse, a missed critical life threatening event.

Some techniques employed in attempt to solve the problem is to make a system that consists of a one lead electrocardiogram (ECG) connected by completing a circuit by two hands. The issue is that the solution relies on the user to take out the device and use it. Other systems, like chest straps or shirts, have their own limitation, such as comfort and affordability. Shirts can cost a fortune for the measurement unit and multiple electrodes. Chest straps are uncomfortable and bulky. Chest straps are similar to wearing a belt but on a user's chest. There is a hump either in the middle of the chest, of the back or in the armpit. It is a challenge to make it discreet.

These techniques may implement a longer period Holter that collects on the case of events. This becomes an issue where a patient is wearing a Holter now instead of for 30 days. Wearing wet electrodes for three days is already uncomfortable enough. Other iterations of a similar system would make this monitor specifically for a user to pull out when they feel like they have an event, but that limits collection to just event data and nothing other than that.

There are some other companies such as Apple™ and Fitbit™ that provide baseline pulse oximetry for BPM with a low degree of accuracy. This does not solve any real heart monitoring issues; they only provide heart rate and nothing more than that. It can potentially be useful for people that want to pay attention to their heart rate while performing physical activities, but that is the one factor that causes for the highest degree of inaccuracy.

There are devices such as Hotter monitors but they are intended more the clinical setting where they collect detailed data, but only for a short period of time. They are the clinical standard; their purpose is to determine what problem a patient might have when they are presumed to have a cardiovascular issue. The system can only be used for 24-48 hours at a time, there are systems that can last for 30 days, but their purpose is typically different. That is mainly for outpatient monitoring. The other issue with this system is their usability. Patients don't enjoy using this system, it is bulky and very uncomfortable.

Devices such as Lifeline are meant for a user to quickly call for emergency response. This solves the problem of having emergency response at your fingertips. The only issue is that it is reliant on the user self-diagnosing and pressing the button when they feel they are in need. It is not the best looking device either. The only real issue they solve is making it easier to call for help, but it doesn't change anything in the interim. You first have to acknowledge you are in distress and decide you need help.

Other existing solutions consist of ECG shirts, phone cases, Apple Watch ECG attachments, a watch to detect if a person has no heart beat, and chest straps. They all have their own pros and cons. Some have the issues where it isn't constantly monitoring, but requires users to sit down and make a measurement. There are some systems that require users to buy an expensive system and additional attachments. Chest straps have never really gained traction due to mainly both how it is worn and how it really looks.

SUMMARY

An example embodiment is a system that includes a fully wireless electrocardiogram (ECG) solution meaning that there are no wires between the electrodes and the base unit, maximizing user comfort and allowing the addition of many more nodes to the system.

An example is a system that includes a nodal network of ECG sensor, so this gives the user the ability to have more or less nodes, and the ability to place the nodes anywhere (to a certain degree, it has to be logical locations).

An example is a system which is a arm-based medical device that uses an on-board cellular system to alert emergency services when the user is in cardiovascular distress. The device takes advantage of newly miniaturized electrocardiograph sensor, pulse oximetry sensors, and mutual reinforcement and anomaly detection algorithms. Abnormal electrocardiograph waveforms are recorded digitally for physician review. In an example embodiment, the system is a heart monitoring system that implements the key concepts of cardiovascular monitoring through pulse oximetry and electrocardiography (ECG). The system implements the key concepts of ECGs and active/capacitive electrodes to produce a wireless network of ECG nodes that can produce a system ranging from 3 to 16 leads.

An example embodiment is a system for monitoring a heart condition, the system comprising: a mobile base unit for positioning on a user and comprising a wireless communication subsystem and a processor; two or more electrode sensors that are conductively isolated from each other, the two or more electrode sensors for wearing on different positions of the user and wirelessly coupled to the base unit, wherein the processor is configured to receive a respective signal from the two or more electrode sensors; wherein the processor is configured to determine heart signal information from the received signals of the two or more electrode sensors, compare the determined heart signal information with expected heart signal information, and transmit a notification when the comparing indicates an abnormal or emergency situation.

In some examples, each of the two or more electrode sensors are configured to be wearable and positionable on different peripherals and/or a chest of the user.

In some examples the base unit is configured to be in communication with a remote monitoring system.

In some examples at least one pulse oximetry sensor is configured to measure pulse oximetry data.

In some examples the processor is configured to transmit the notification to a remote monitoring system when a change above a defined threshold indicating the abnormal or emergency situation is detected by the processor.

In some examples the threshold comprises a combined threshold of heart signal data and pulse oximetry data.

In some examples the transmitting the notification comprises sending the notification according to a defined priority list of remote users.

In some examples the transmitting the notification to the defined priority list of remote users comprises transmitting a first notification to Emergency Medical Services (EMS), transmitting a second notification to a designated family member or plurality of family members, transmitting a third notification to a close neighbour, and transmitting a fourth notification to a patient file for an issuing doctor.

In some examples the first, second, third and fourth notifications are first acknowledged by the user before being sent.

In some examples a Global Positioning System (GPS) and/or a cell tower triangulation system are configured to determine a location of the system.

In some examples transmitting the location of the system to a remote monitoring system according to a detected emergency situation.

In some examples the two or more electrode sensors each include a dry capacitive contact electrode.

In some examples the two or more electrode sensors are configured to be positionable at different positions to for determining a differential signal across a heart of the user.

In some examples at least one of the two or more sensors are conductively isolated from the base unit.

In some examples at least one of the electrode sensors, at least two of the electrode sensors, the base unit, and/or another device, are configured to insert a DC bias signal to the user, in order to producing a comparable reference voltage onto the user for the determining of the heart signal information.

In some examples a voltage value of the DC bias signal is commonly known by the two or more electrodes and the base unit.

In some examples a voltage value of the DC bias signal is known by the base unit.

In some examples one or more accelerometers for detecting motion data of the user, wherein the processor is configured to ignore data from at least one of the electrode sensors when motion data of the user exceeds a motion threshold.

In some examples determining of the heart signal information comprises constructing a electrocardiogram (ECG) signal of a heart of the user.

In some examples the processor is configured to store the received heart signal information from the two or more electrode sensors to a memory.

In some examples the defined priority list of remote users comprises at least one of Emergency Medical Services (EMS), a designated family member, a plurality of family members, a close neighbour, or a doctor.

In some examples the base unit comprises one of the electrode sensors.

In some examples there are one or more feedback circuits, each feedback circuit configured to determine localized noise at the respective position on the user of one of the electrode sensors user, and each feedback circuit configured to insert a voltage signal to the position of the user to suppress or cancel the determined noise.

In some examples the one or more feedback circuits comprises two or more feedback circuits, each feedback circuit configured to co-ordinate the inserted voltage signal from all of the feedback circuits as a common signal.

In some examples each of the feedback circuits comprise a right leg drive (RLD) circuit.

In some examples there is disclosed a method of monitoring a heart condition comprising: positioning two or more electrode sensors on different positions of a user, the two or more electrode sensors being conductively isolated from each other; positioning a base unit on the user, the two or more electrode sensors wirelessly coupled to the base unit; receiving, by the base unit, a respective signal from the two or more electrode sensors; determining, by the base unit, heart signal information from the received signals of the two or more electrode sensors; comparing, by the base unit, the determined heart signal information with expected heart signal information; and transmitting, by the base unit, a notification when the comparing indicates an abnormal or emergency situation.

In some examples there is disclosed storing the received heart signal information to a memory.

BRIEF DESCRIPTION OF THE DRAWINGS

Reference will now be made, by way of example, to the accompanying drawings which show example embodiments of the present application, and in which.

Similar reference numerals may have been used in different figures to denote similar components.

DETAILED DESCRIPTION OF EXAMPLE EMBODIMENTS

In example embodiments, the system is an emergency response for cardiovascular patients. The system can be used to collect 24/7 user data to monitor for and determine when there is a cardiovascular issue. If there is an issue where emergency response is needed, the system will send a notification to contact help for the patient. In example embodiments, if the system determines that there is not a major issue but simply an irregularity, it will save the data to a memory. In an example embodiment, the saved data may be used for analytics.

Figure 1:
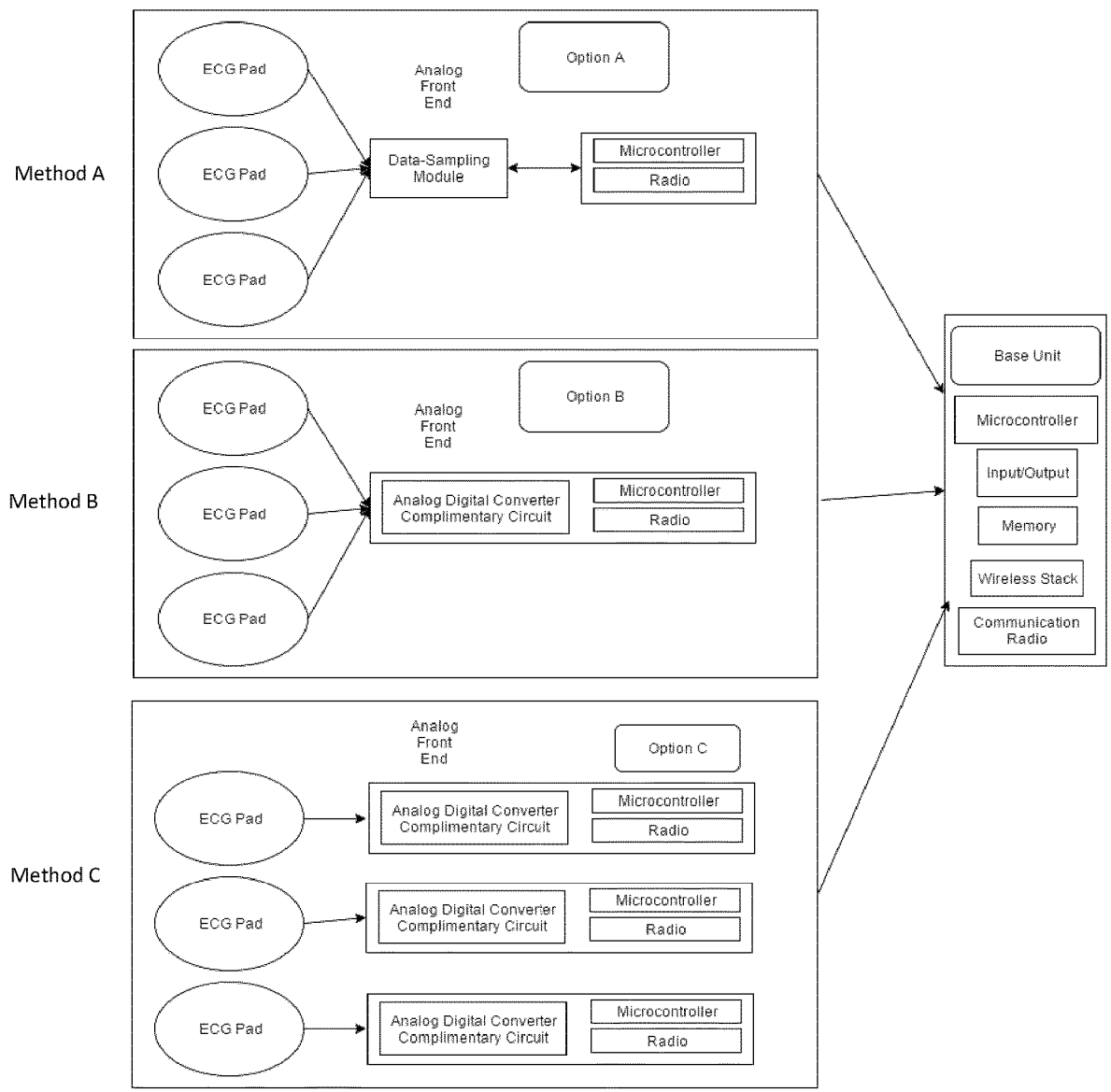
FIG. 1 discloses three example different ways to collect an ECG.

With reference to FIG. 1, there is disclosed three different ways to collect an ECG, in accordance with example embodiments. As disclosed in FIG. 1, Method A provides one example way of collecting an ECG. Method B discloses an alternative example embodiment of collecting an ECG. Method C maximizes patient comfort and allows for great flexibility, in an example embodiment.

In example Method C, the ECG electrodes are capacitive electrodes. The ADC (Analog to Digital Converter) is of high quality. In example embodiments, the ADC is producing a large amount of data to be sent over wireless. In example Method C, an example advantage of this specific application is that there is no need for a live data transfer, rather there can be a time delay for data to be received by the base station. For example, data may get to the base station a couple seconds after collection.

Figure 2:
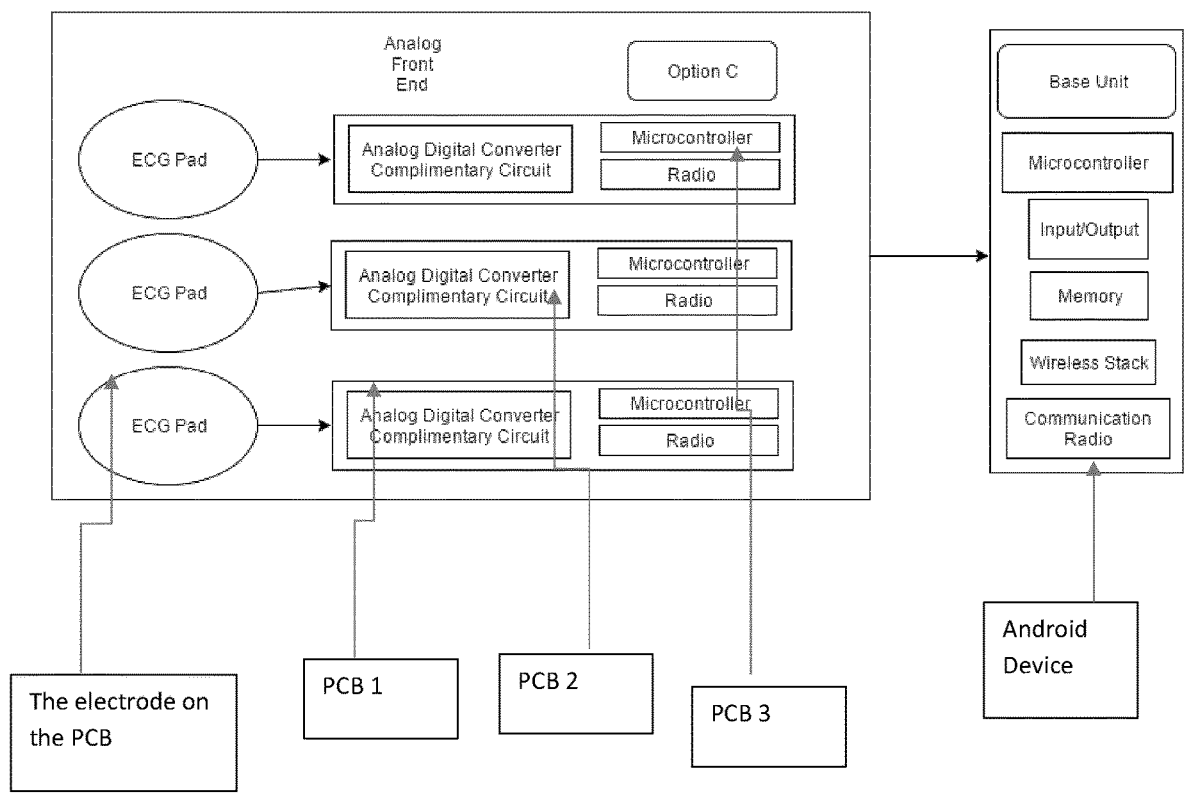
FIG. 2 discloses a further detailed view of the third way of data collection of FIG. 1.

With reference to FIG. 2, a further detailed view of Method C is disclosed.

In some examples, for the system function, there is provided three devices. More than three devices or fewer than three devices may be provided. In FIG. 2, there are three devices that are provided in coupled communication to one phone. The three devices may have identical boards with all the same components. In some examples, the three devices are synced to the same time for matching of data. This is one set of possible combination of sensor nodes to produce an ECG where all nodes are made the same.

In an example embodiment, the system can operate with a minimum of two nodes. In some examples, with reference to FIGS. 3 and 4, the minimum for good data quality is three nodes. Additional nodes may be added to the system to increase the system's level of data quality.

In example embodiments, sensors are conductively isolated. In some example embodiments, the sensors are not conductively connected to each other. Further, in some example embodiments, the sensors are not conductively connected to the base unit, or to ground. Further, in example embodiments, the sensors do not require conductive leads or wires for any such interconnections when the sensors are each individually connected to the patient.

Figure 3:
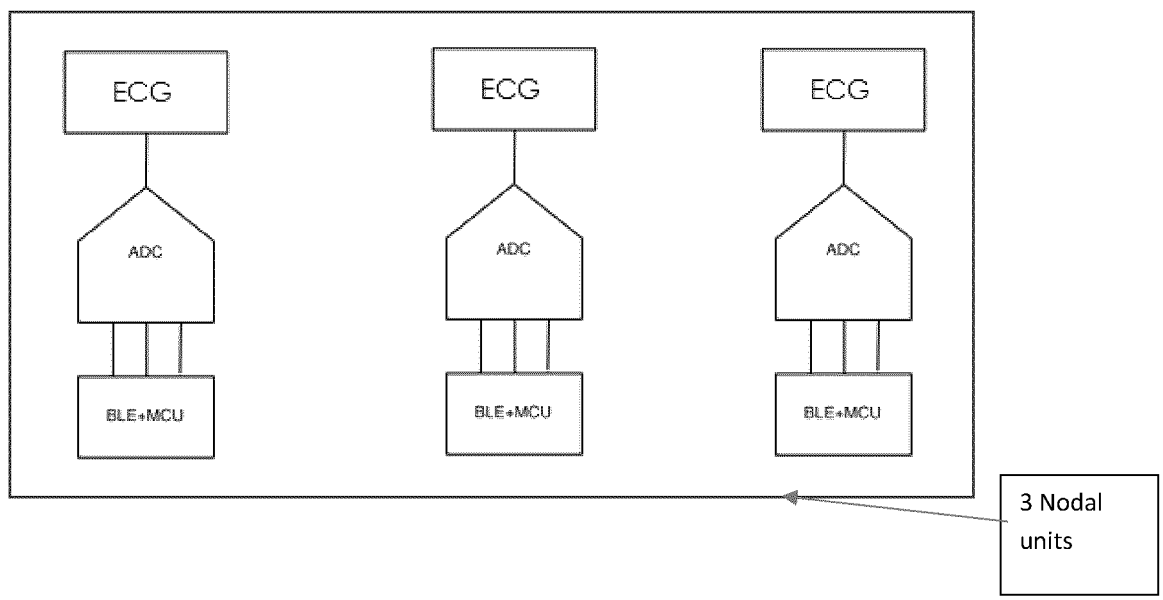
FIG. 3 discloses three nodes for data collection.
Figure 4:
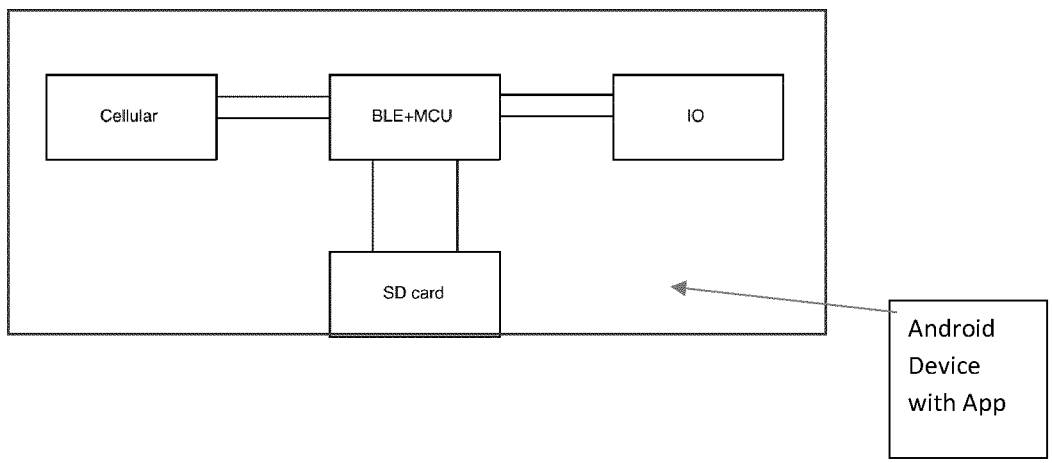
FIG. 4 discloses a simplified example embodiment of FIG. 3.

With further reference to FIG. 4, there is provided a simplified example configuration compared to the configuration provided in FIG. 3. The example configuration includes Bluetooth Low Energy (BLE) wireless MCUs (MicroController Units).

Figure 5:
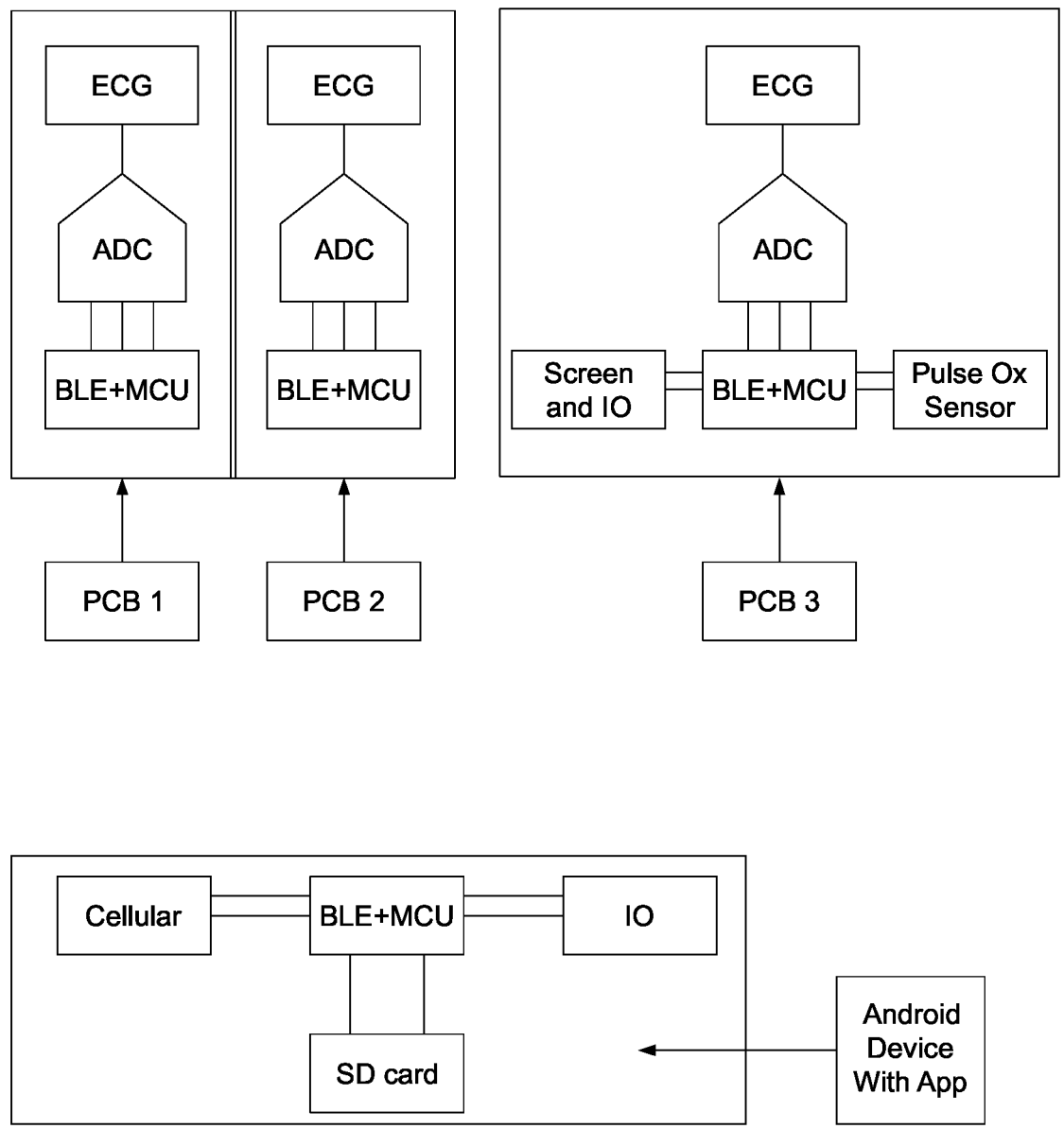
FIG. 5 discloses a node with increased functionality.

With reference to FIG. 5, a further example system configuration is provided. In this example configuration, all units have the same core parts, but one node is made differently with more functionality and method for the user to interact with the system. The example configuration allows for additional functionality to the device. Devices can have additional sensors such as pulse oximeters and/or accelerometers and/or temperature sensors. There can be additional IO (Input/Output user interface) for user interaction with the device.

Example embodiments of the system may allow for an increased level of data quality and flexibility. An example goal of the system is to provide the user with holistic data or multiple metrics on their health while providing flexibility and comfort on how the device may be worn.

In an example embodiment, dry/capacitive/active electrodes are used instead of wet electrodes. In this example, there is no wet adhesive, and the dry/capacitive/active electrodes can be reused. These electrodes may contribute to a more comfortable device.

Another example benefit of the system is that it may provide more holistic cardiovascular data for doctors and clinicians to use because the device implements a nodal system that allows for flexibility and usability. Providing more holistic data to a clinician may allow for better treatment of heart health.

Another example value of the system is in providing data about the user's cardiovascular condition that was otherwise not easily obtainable. Example data that may be provided is a user's baseline heart health up to and including data collected during critical events. Providing valuable data such as a baseline data allows a clinicians to understand what a "normal" baseline condition is and if the user's current condition is concerning. This can also provide valuable information such as data pertaining to what happened at the start of an event. All of these pieces of data provide valuable information in the treatment of a patient.

From the user's perspective, an example value is in having a wearable system that is used to help the user monitor their health. The user may be provided with numerous biometrics immediately with sensor variety, ease of use, in a form factor that is meant to integrate seamlessly into the user's medical system.

The table below outlines example values of the system.

TABLE 1

| Value prop for | Specific Value |
| --- | --- |
| User | Peace of mind |
|  | Data at their fingertips |
|  | Cost-effective |

TABLE 1-continued

| Value prop for | Specific Value |
| --- | --- |
| Clinicians | Anomaly detection |
|  | Recommendations for emergency response |
|  | Location tracking for emergency response |
|  | Gives clinicians the data they don't have |
|  | More clinical grade sensors in one device to better diagnose irregularities |
| Hospitals | Low-cost, easy-to-implement system |
|  | Gets patients through the system quicker |
|  | Reduces and cuts cost for hospitals |
| Pharmaceutical Companies | Creates valuable data for drug development |
|  | Trend assessment for advertising purposes |
| Insurance Companies | Alleviates risk |
|  | Generates statistics about population |
|  | Trend assessment for advertising purposes |
| Family of user | Peace of mind |
|  | Notifications of issues to address |

Example features of the example system include:
For the user:
24/7 monitoring
Non-invasive monitoring
Pulse oximetry measurements
ECG measurements
Emergency response
Event data collection
Notification of current cardiac and user health
Data storage for long term review
Connectivity to a phone or a base unit
Fall detection
Event diary
Record of short medical history
User and clinician access to data
A base unit, for example, a mobile phone, computer wristband, computer watch, computer wristband or smartwatch
For the hospital:
Access to data using to an easy-to-implement system
ECG and Pulse Ox summaries
Get the patient to the right doctor quickly
For the family of the user
Notifications of emergency events
Notifications of recommended check-ups
The following are further specifications of the system, in some example embodiments:
Intuitive System
Must be able to contact help when needed
Record events that are detected
Record events that are user-triggered
Must integrate with ER systems & EMS vehicles
Must not interfere with daily life
Device must be non-invasive
Must store medical information of user
Can run for 24 hours a day
Durable to last a minimum of 2 years
The device must pass regulatory standards around the world
The device must meet a certain level of reliability
Additional features of example embodiments of the system will now be described.

A Wearable Electrocardiograph: The system includes a bracelet, wristband, or arm wearable connector. Arm based electrocardiographic analysis is typically seen as being too noise filled to provide a valid method of clinical cardiovascular analysis, and wet electrodes cannot be used as an around the clock solution due to irritation. Example embodiments of the system can be of silver chloride biomedical, dry/capacitive electrodes, positioned equidistant around a user's wrist, processed through a custom printed circuit board, designed to reduce noise and human impedance upon the system. A noise optimized circuit board alleviates the technical flaws of wristed based ECGs.

Integration into the Medical System: To increase a patient's likelihood of survival, the system can seamlessly incorporate into the medical system. The system's on board SIM card, allows the capability to directly contact emergency services when a user is in cardiovascular distress. The system can also aid the emergency medical service workers it contacts to be superior to its competition. For both reasons of security concerns for the patients' medical data, and to assure doctors do not require more training in order to utilize the device, the system is configured to print all of the data emergency physicians may need via an emergency room wireless printer. To satisfy this, the system translates months of a user's cardiovascular history, into a brief summary which resembles existent Holter reports, to be printed for physician use upon arrival in the emergency room. This alleviates the need for an emergency room physician or emergency services professional to delay the patient's treatment by placing them on an ECG monitor. The system can allow a patient to be immediately transferred into the facility of cardiology upon their arrival in the emergency room. This will not only reduce the costly effects of late response to heart related illness, but it will also increase the chance of saving the patient's life. All of this data can be utilized by the medical system.

The example system provides accurately recorded data for any irregular event of the time of the occurrence that occurrence that can be passed to healthcare clinicians. Due to the access to data collected from the time of the event, the success percentage of the patient leaving the event with no harm increases. Additionally, clinicians can better diagnose and treat their patients, and hospitals can more quickly process patients through hospital systems.

The nature of the system is a portable around the clock non-invasive heart monitoring system that can contact help whenever it is needed, with additional features. What this means is that the system is compact enough to bring anywhere, and have widespread cellular service. The system can be efficient to save system resources. It can be power efficient enough to last at least 1 day since the system is aimed to have around the clock monitoring for the user. The system can also be designed in a cost effective manner so to make it affordable and accessible. All materials must be chosen with environmental impact and to be biocompatible as a major design consideration. The system utilizes biometrics such as pulse oximetry, ECG, and movement data, as well as its onboard analytic algorithm to determine when the user is in distress.

Standalone: One consideration in making the device is to fit the needs of the user population. The user of the device can be Baby Boomers. Baby Boomers typically have a hard time using complex technical devices such as smartphones and smartwatches. This means that the system can operate independently to connect to another device to avoid adding more complexity for the user. Thus the system may be standalone, minimalistic, and require only a simple set of use instructions for the user, in order to be optimal for the intended market.

Contacts: There are two main issues with skin contact with pulse oximetry sensors, when the sensor is not touching the skin, and when the sensor is pushed against the skin too hard. Issues arise when the sensor is too far away from the skin and it cannot properly reflect or receive incoming light. The second issue is when the sensor is pushed against the skin and the blood in the capillaries is pushed out so the sensor cannot receive a signal that there is blood present. ECG sensor require skin contact. Contact issues are not present in wet electrodes because of the stick adhesive, however dry electrodes can still be lifted off the skin, and additional residue can remain on the electrode adding additional impedance Power Consumption: Power is a major issue with any kind of mobile/wearable device. Batteries come in many different forms, which either makes it easier to charge, contain more capacity, or more chemical stability. Even with limitations in the field of energy storage, if the system is made to be efficient, battery storage becomes a minimized issue. The component in the system that consumes the most energy is the pulse oximetry sensor because of the green LED it utilizes. It is due to this that the pulse oximetry sensor cannot be active at all points in time. Realistically to save power means to set the system engage in moments of distress. This allows us to attain holistic data sets on the user only when required. As the pulse oximetry data can engage as a supplement to the ECG data, once an error has been detected.

Movement Filtering: Many issues arise with excessive movement of the human body. The sensors are unable to collect data, or they are picking up a lot of noise with the data. Pulse oximetry is susceptible to a lot of inaccurate data due to the fact that if the sensor is shifted it will pick up the green light differently. This causes for the sensor to pick up different and inaccurate readings. The issue with movement of the human body for the ECG sensor is that it will pick up muscle contractions. Muscles contract due to electrical signals, similar to that of ECGs, and depending on where the electrodes are placed, the muscle electrical signals can overcome the signals from the heart. This adds more noise to already noise filled data. In the case of intense movement of the human body, the accelerometer will pick this up and will instead compensate for any kind of inaccurate data.

Pulse oximetry noise filtering: The pulse oximetry has hardware based anti aliasing and noise filtering on the board already, this both eliminates noise and smooths the data. The pulse oximetry has an active filtering process to reduce the magnitude of any unwanted data, and increase the intensity of critical data. Once the data is filtered and amplified the analog logic of the sensor is converted into digital signals to be processed by a microcontroller. There is minimal filtering on the program itself to reduce stress on the microcontroller. The only job of the microcontroller for the pulse oximetry sensor is to run it through the algorithm to determine if it is good or not. In the case of intensive movement, pulse oximetry data is highly inaccurate. Movement intensity is recorded and determined based on the accelerometer.

Memory recording: Memory storage is based off of a removable solid state memory. Having removable memory means that it can be stored for a long time, especially solid state, this means that there is no need for the system to erase data if it is not needed. The system will also not be recording every single second of data, in an example embodiment. It will only store segments of normal data, and irregular data in a simplified example embodiment, and raw data for emergency situation where raw data is critical. In another example embodiment, the memory comprises external memory storage. Since the system can have an embedded cellular communication subsystem, this allows for connectivity with a potential external storage system. The external system allows for more processing, larger storage areas and compliments the system by providing more metrics from the data.

Figure 28:
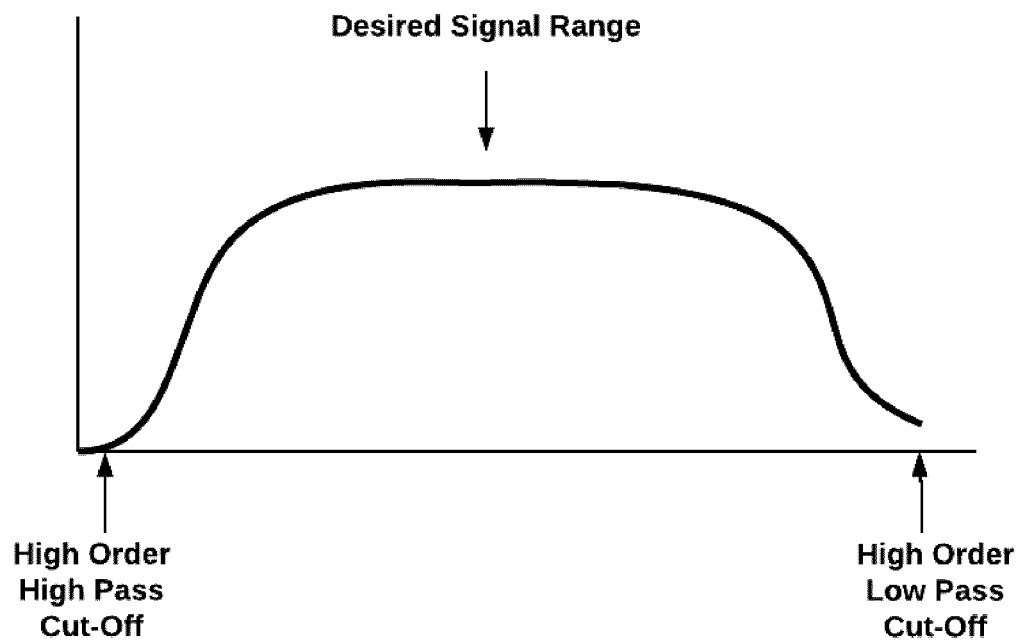
FIG. 28 is an example graph disclosing a desired signal range.
Figure 29:
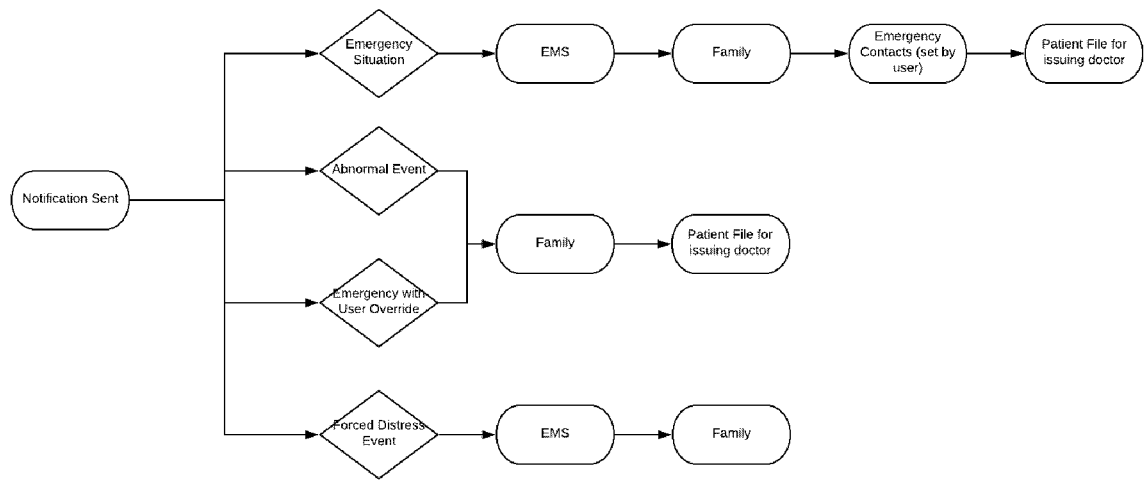
FIG. 29 is an example flowchart of sending a notification based on a hierarchy of priorities.
Figure 30:
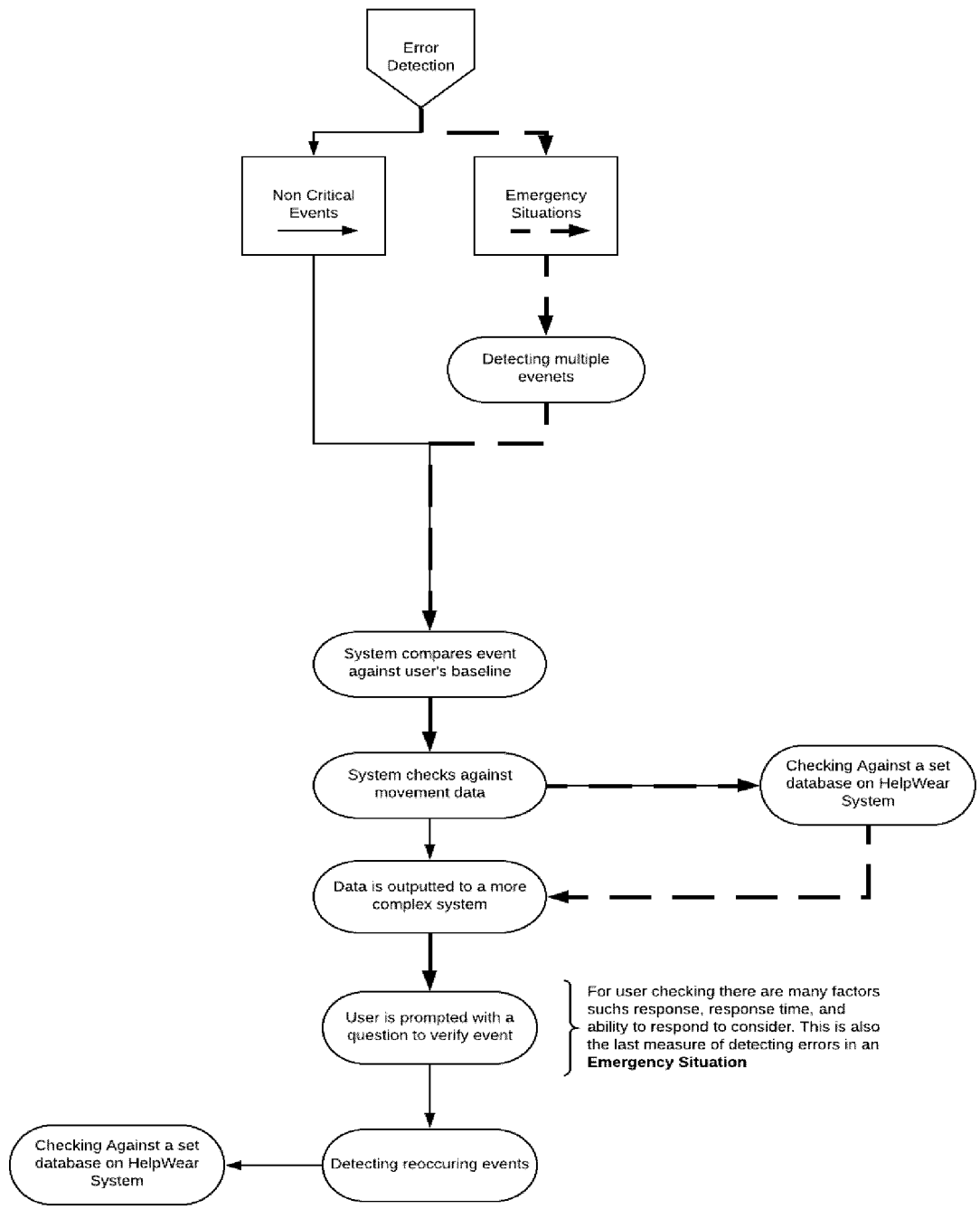
FIG. 30 is an example flowchart of detecting errors and setting a baseline of normal events.
Figure 31:
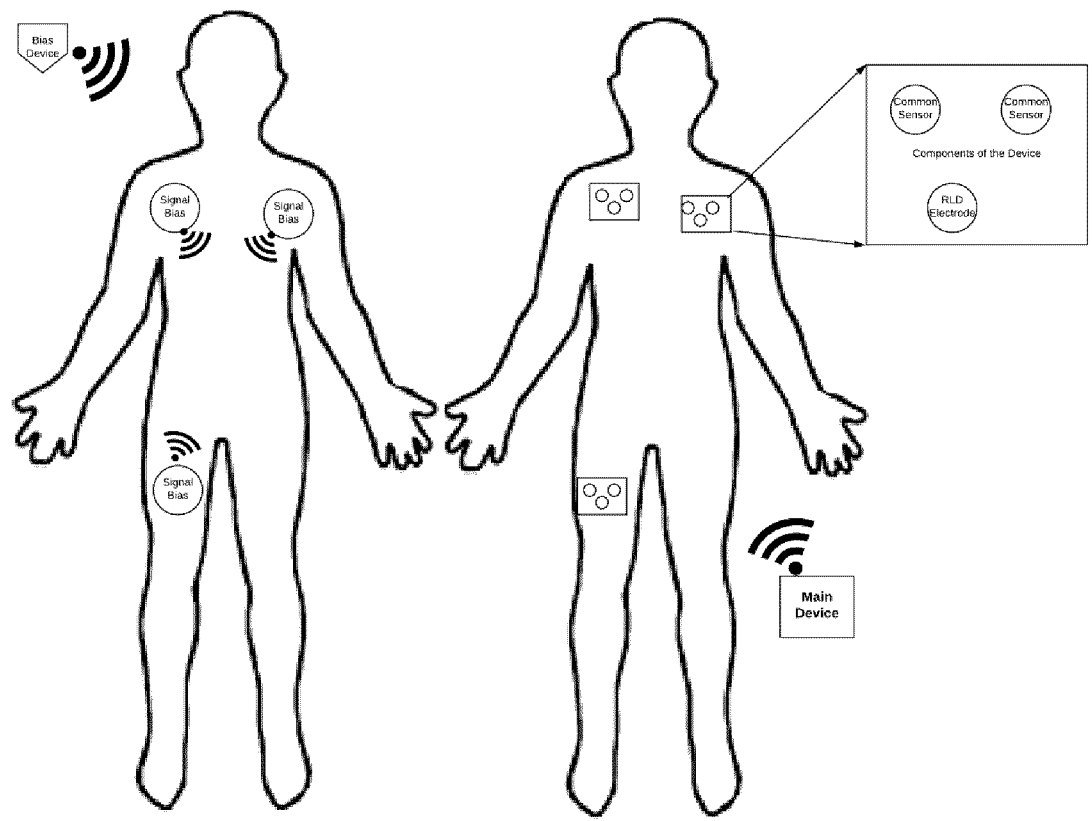
FIG. 31 is an example diagram of sensors positioned on a user and wirelessly communicating with a remote device.
Figure 32:
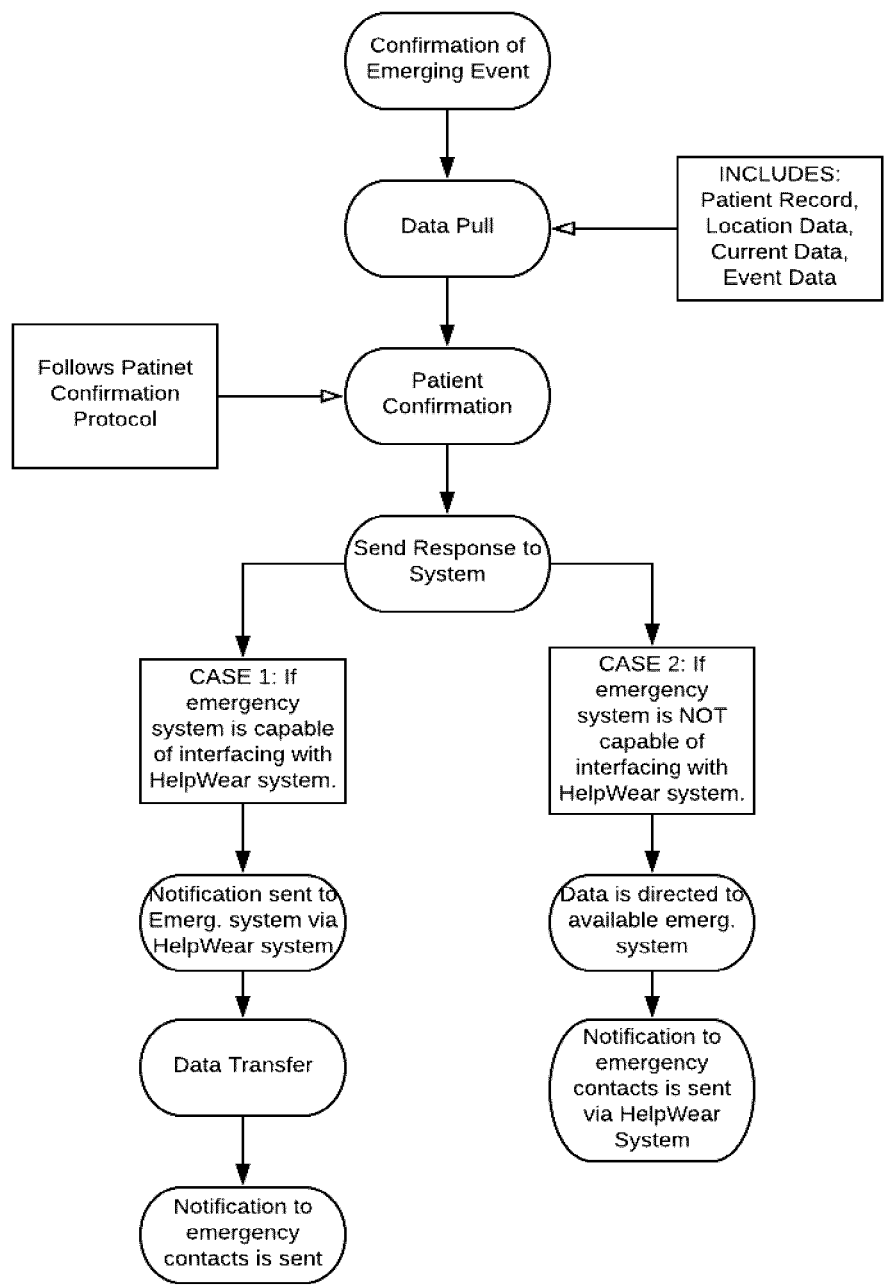
FIG. 32 is an example flowchart of detection of an emergency event and sending a notification of the emergency event.
Figure 33:
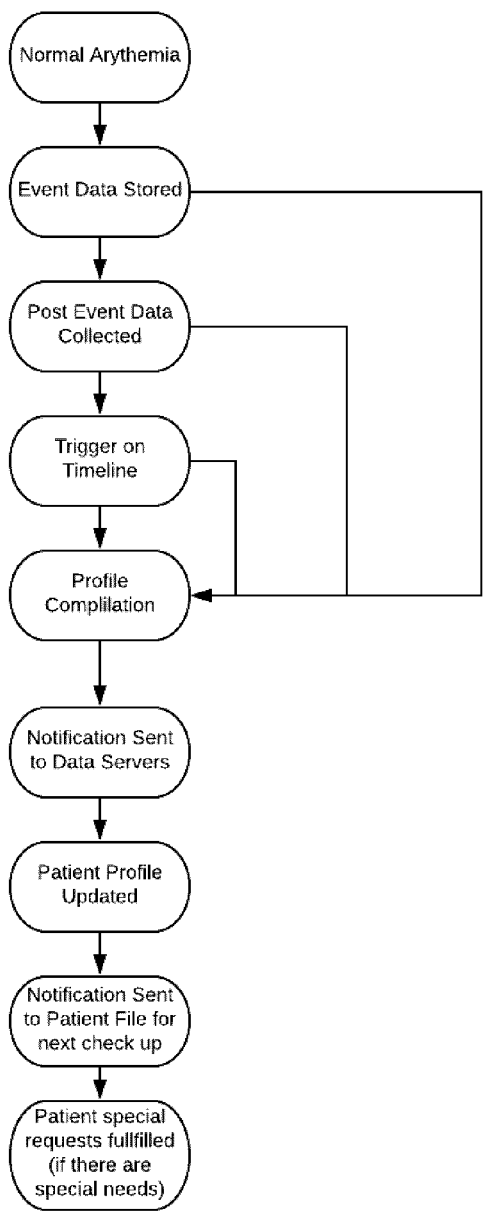
FIG. 33 is an example flow chart of a detection of an normal arrhythmia and storing data of an event.
Figure 34:
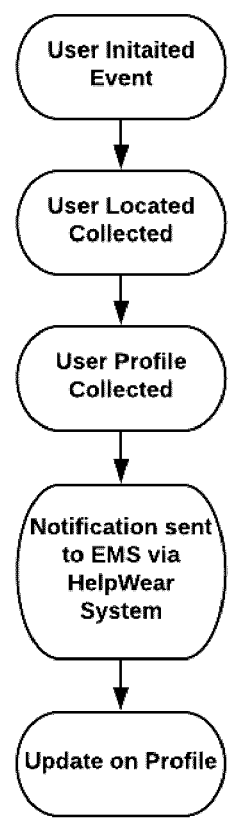
FIG. 34 is an example flow chart of a user initiated event including a notification sent to EMS.

Data filtering ECG stage: A large portion of the data collected may be inherently noise. To filter out the noise means to eliminate data from the raw data collected from the electrodes. The collected data may, in example embodiments, be received at a rate of every 4 ms, or 250 samples per second. Once the data is collected from the electrodes the data is transmitted through a hardware-based filter. In example embodiments, the hardware-based filter will filter out noise specifically around the 60 Hz range, and anything below the 0.5 Hz range and anything above a 30 Hz range, as referenced in FIG. 28. In example embodiments, a user may encounter high energy power lines that run at a 60 Hz range. This may start to add noise, because the signals from the data is very low voltage. In example embodiments, the typical heart should not be outputting anything lower than 0.5 Hz. Therefore, anything below 0.5 Hz is considered noise. Further, the heart should not be outputting anything above 30 Hz as that is too fast. There are other certain ranges of frequencies that are considered to be noise, determined by the on board analytic algorithm, so to not eliminate important data.

In example embodiments, after all the hardware filtering is done the intensity of the signal is still very weak, so the analog signal of the data is amplified. Once the signal is amplified it goes through an analog to digital converter so everything is in a digital format to be processed by a microcontroller, as disclosed in FIG. 3.

Data acquisition ECG stage: Acquiring the data that is filtered and ready to be processed is critical. Microcontrollers cannot process analog signals since it is a digital based system. This is where the use of an analog to digital converter (ADC) is implemented. In the real world an ADC may not be ideal, due to this a conversion from an ADC noise may be produced. This problem is mainly due to aliasing in the data meaning that the data comes in more blocky forms, or something like a pulse width modulation output. To solve this issue antialiasing is used. This is done by an antialiasing filter that can convert blockly data into smooth curves and continuous lines, unless the data proves otherwise like ECG peaks.

Test Cases: There are two main example cases of what information the data can provide about the user: either the data provides information of normal or irregular patterns. In the case of normal patterns, data will be displayed on a screen for the user to understand their current state or current heart condition. In the case of normal data, only segments on the normal data is recorded. Irregular patterns can include an analysis of the waveforms. In the case of irregular data there are two methods of classifying it. It will either be classified as irregular non dangerous, or irregular dangerous. If the irregularity is proven to be non dangerous a message is sent to the caregiver of the user as a notification, and data is collected of the event that occurred. If the data proves to be dangerous than a distress message is sent out to both the caregiver and emergency services, raw data of the event that occurred is stored, if medical professionals need to see every single detail of the event.

Further, there is also provided another test case, where the user falls. If the user falls, an example situation is a possible cardiac event, or just a normal trip and fall. The system will detect a fall and if the user is unable to perform the consciousness test soon after falling. This is an example case of emergency and a distress message will be sent out. If the user does respond to the consciousness test the system will disable and not call for emergency services, but will mark down or store in memory information pertaining to when the event occurred.

Data Acquisition Rate: Due to the inherit nature of the device collection of raw data comes at a rate of above or equal to 1500 Hz. The signal can be optimized in program to both decreasing signal sample rate, but increasing signal accuracy, for example.

First Example Embodiment

Figure 6:
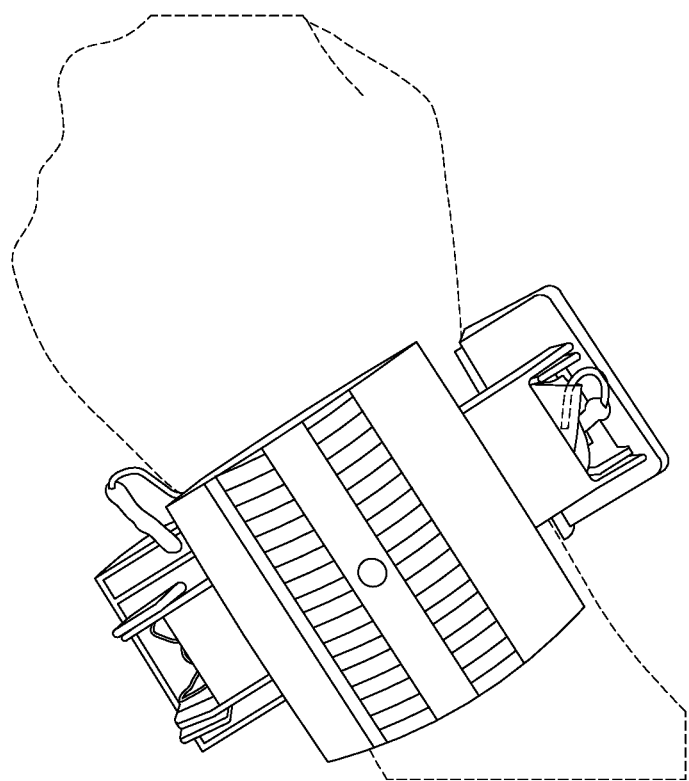
FIG. 6 is an image of an example wristband casing.

In some examples, an example device is able to detect a heartbeat of the user, and when the heartbeat goes out of a certain bound or threshold it will trigger a signal. The device used off the shelf components like Arduino and breakout boards, in an example embodiment. In some examples, the device includes a pulse oximetry sensor, energy storage, a microcontroller, and a communication module. The device did simple analytics to demonstrate that when the system sees there is a problem a caregiver can be told about the issue to respond accordingly. FIG. 6 discloses that there are three blocks to the example device, and this is due to the fact that there are many bulky components in some examples.

With further reference to FIG. 6, an example embodiment of the system is disclosed. An example watch casing is made by 3D printing Second Example Embodiment An additional example embodiment is a smaller version of the first example embodiment. It could do everything that the first iteration could do in a smaller package. This example system demonstrated that there is a need for a more powerful microcontroller to do all the required tasks.

Figure 7:
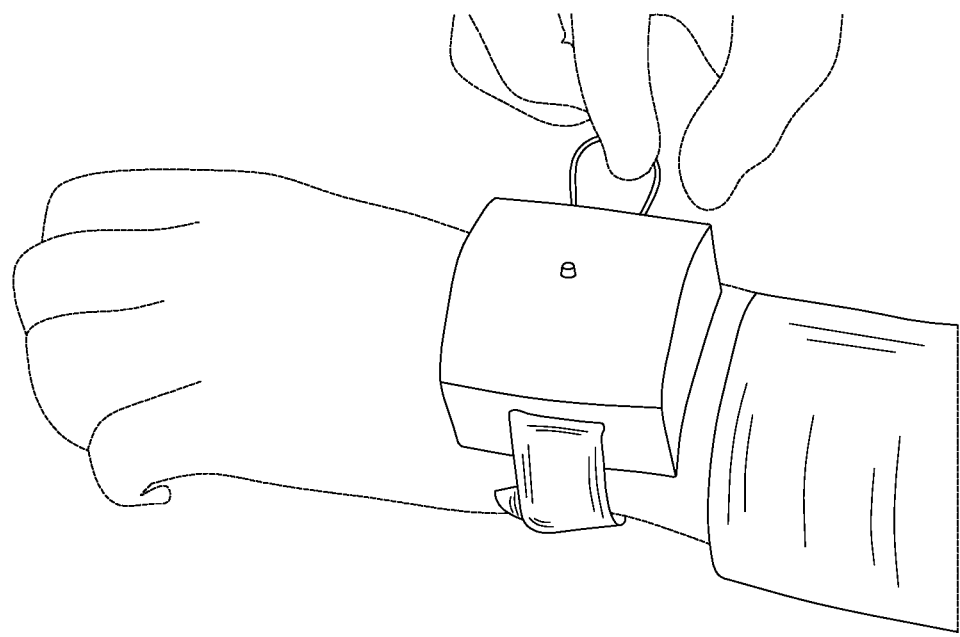
FIG. 7 is an image of an alternative example wristband casing.

With reference to FIG. 7, a second example embodiment of the system is disclosed. The watch casing is made by 3D printing with off the shelf components like the first example embodiment, but smaller.

Third Example Embodiment

The third example embodiment made the entire system completely smaller.

This revision added a screen and a watch face for the user. This iteration also includes many new sensors and the best possible off the shelf microcontroller that can give the system to do the intended analytics to know when there is an emergency.

Figure 8:
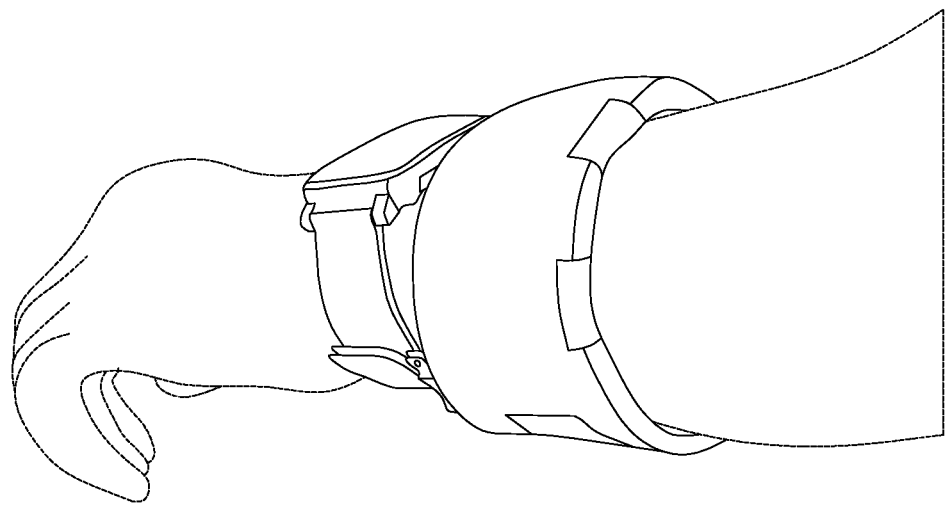
FIG. 8 is an image of an alternative example double wristband structure, where one wristband includes all the sensors and the other wristband does the processing.

With reference to FIG. 8, a third example embodiment of the system is disclosed. The example watch uses a two cuff system. One cuff includes all the sensors and the other cuff does the processing.

Fourth Example Embodiment

The fourth example embodiment is an improvement of the third example embodiment. This example embodiment takes the two cuff system of the third example embodiment and makes it all into one, it can do everything the third example embodiment did, but in a much smaller form factor.

Fifth Example Embodiment

Figure 9:
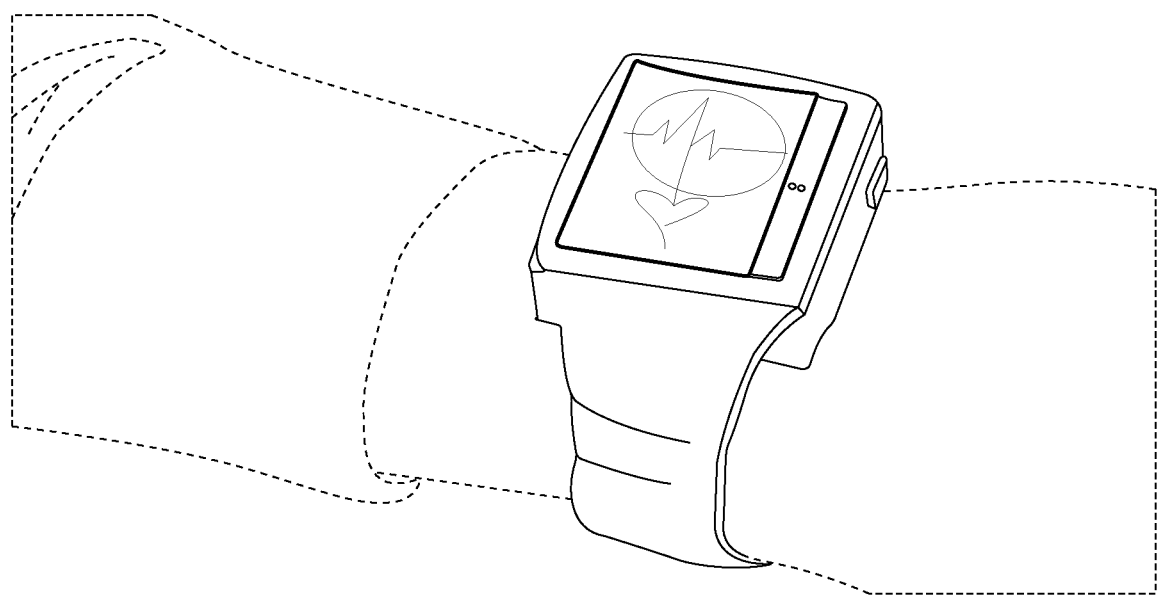
FIG. 9 is an image of an alternative example wristband in which the wristband is a standalone device.

With reference to FIG. 9, a fifth example embodiment is disclosed. This is a completely standalone device. The mock up is a 3D printed encasing to demonstrate size, shape and texture.

Figure 10:
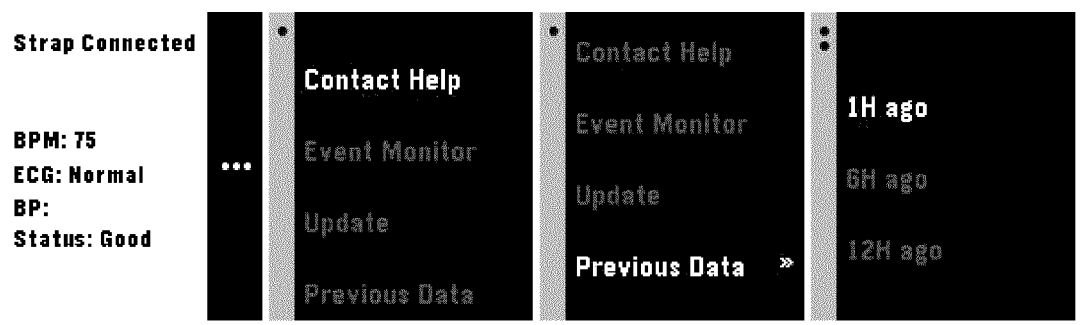
FIG. 10 is an example graphical user interface of a demonstration of the device's test screen viewed through a Pebble™ watch.

Utilizing the Pebble™:

A pre-constructed smartwatch base may be used, that contained an easy to access data port, an open source software development kit (SDK), and flexibility in manipulating the system's hardware and software components. The Pebble™ watch is a consumer grade smartwatch that connects to a smartphone to have access to advanced processing and apps on a wrist. Pebble™'s open source SDK allowed for the development of advanced applications on the watch. It acts as a hardware based extension of the Pebble™ watch and allows for the flexibility of connecting to a phone, an exterior MCU, and a viewing environment for the programmer. A demonstration of the device's test screen viewed through the Pebble™ is seen in FIG. 10.

Figure 11:
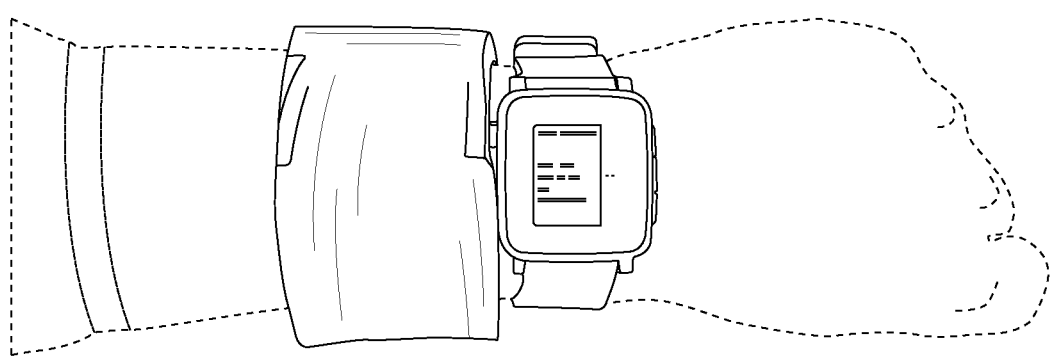
FIG. 11 is an image of alternative example embodiment using a Pebble™ device on a wrist of a user.

The system using the Pebble™ device is disclosed in FIG. 11, on the wrist of a user. Note the system includes both the Pebble™ watch and a strap, which contains the desired sensors.

Primary Pulse Oximetry Data Processing:

The example pulse oximetry sensor in the example system required minimal refining, as the hardware was designed to perform onboard filtering to eliminate noise. Pulse oximetry is ideal in a situation where the user is motionless, otherwise it is ineffective as a technical sensor under the effect of movement. When a patient is in motion, the light emitting diode is also in a state of motion. Thus, as the patient moves, the algorithm attempts to attain its biometrics based off of data collected from a large variety of blood capillaries, assumed to be a single set of capillaries. It is due to this technical restriction that consumer wearable pulse oximetry based sensors are unable to attain accurate data sets. However by adding a fine tuned technical accelerometer to the system, it is possible to determine when the device is in a state of even slight movement. This allows the algorithm to compensate for any irregularities, which may be otherwise falsified in other technical systems.

Figure 12:
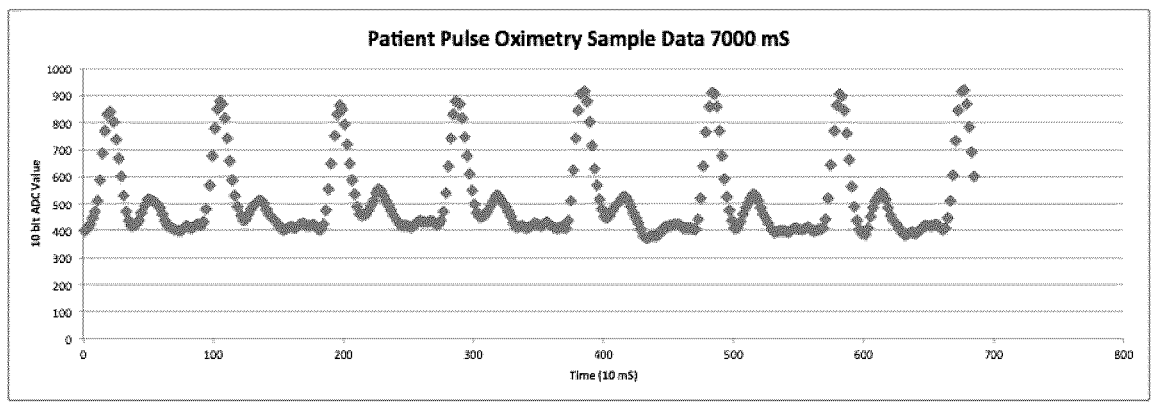
FIG. 12 is an example graph of example pulse oximetry readings obtained from a healthy patient.

FIG. 12 discloses an example of the pulse oximetry readings obtained from a healthy patient, which demonstrates cardiovascular normality. The data set seen in FIG. 12 is the data collected from the pulse oximetry sensor in the system. This data did not need to be filtered by a software algorithm due to the hardware anti-aliasing available in the component. Cardiovascular trends are inherently cyclic, consistent and predictable. The pulse oximetry data presented is valuable, but must be correlated with electrocardiographic data to attain optimal results.

Figure 13:
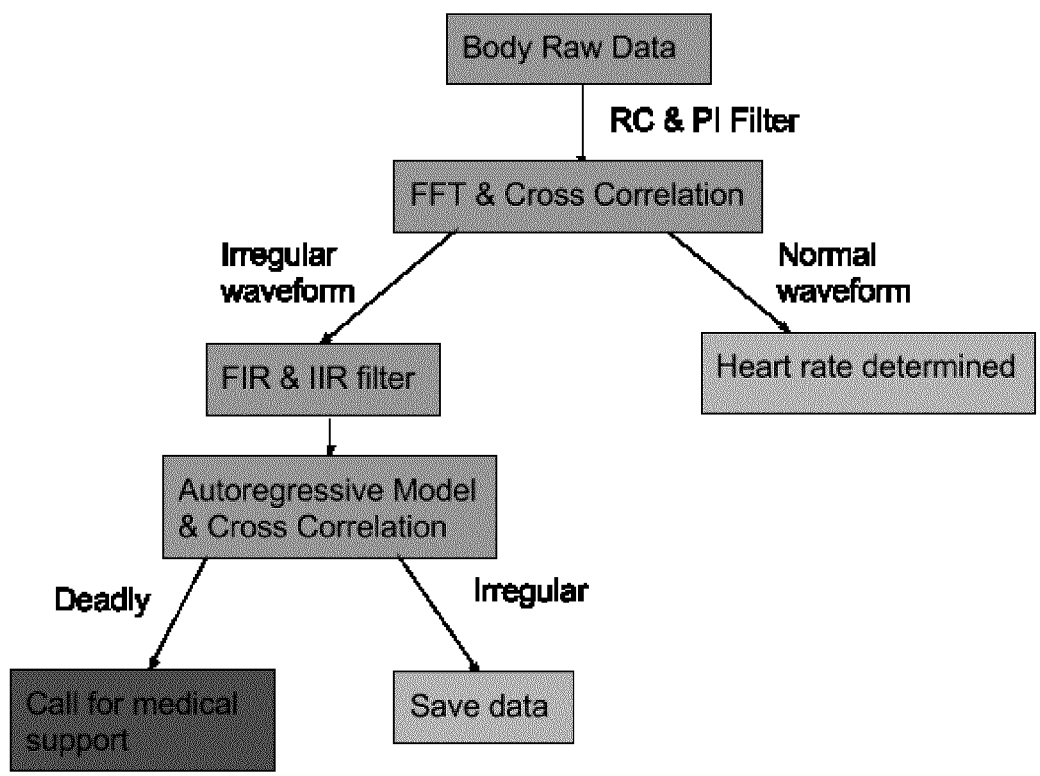
FIG. 13 is an example flowchart of an example systems analytic process including receiving data from a user, filtering the data and saving the data to a memory.

System Analytics:

An example systems analytic process is outlined in the flowchart disclosed in FIG. 13. When the system receives input from the human body the data goes through a preliminary filter via the hardware. The hardware implements a PI or RC filter with the onboard ADS1298 anti aliasing. PI and RC filters are hardware based filters made by an arrangement of resistors and capacitors, which then smooths the data set. The system will then output data in hexadecimal form with plus and minus (224–1) possible values. The decimal values are then converted into decimal code before being stored in an array. This array is processed through a Fast Fourier Transform (FFT) where the data is filtered in order to allow for a cross correlation process to occur. The FFT arranges the data into an amplitude vs frequency domain to filter out unneeded data. The filtered data is then placed through a cross correlation process where the system will compare standardized data sets and the electrocardiographic waveforms obtained by the systems ECG in order to identify any irregularities. If the system reads the cross correlation factor to be very similar to a normal ECG the data will not be saved. If the system reads the cross correlation factor to vary from the standardized ECG the data will enter a more intensive smoothing algorithm. The Finite Impulse Response and Infinite Impulse Filter will be used in combination and an Autoregressive Model will be used to smooth out the ECG based on the last value within the ECG, rather than a FFT as a high pass filter. Once the data is filter by the Autoregressive Model it will start to cross correlate emergency level ECG data with the filtered user ECG. If the system deems that the user is in distress it will contact the caregiver of the user. If the system deems the user does not need immediate assistance it will book mark the event and save it in data storage. If the event is deemed to be an emergency, the raw unfiltered data is stored for analysis by a clinical cardiovascular technician. A more accurate measure of heart rate is determined by finding an ECG waveform peak, and the next ECG waveform peak, and calculating the heart rate. The system will find blood pressure by calibrating itself with the user using a proprietary comparative algorithm.

Example embodiments of the system are designed to improve cardiovascular monitoring for all people who may require it, not only to act as an emergency response device. The system's non-invasive nature, and lack of geographic restriction with usage, cardiology patients can now monitor their heart health in a way that is thorough, and does not interfere with day to day life. Providing an example solution that not only improves the cardiovascular diagnosis and care process for the patients, but also aids in making patient care more efficient, contributes to relieving stress on the medical system.

A patient's heart rate, electrocardiographic rhythm, blood pressure and blood oxygen levels, are needed to make a diagnosis. These can be measured by a variety of techniques described below.

Figure 14:
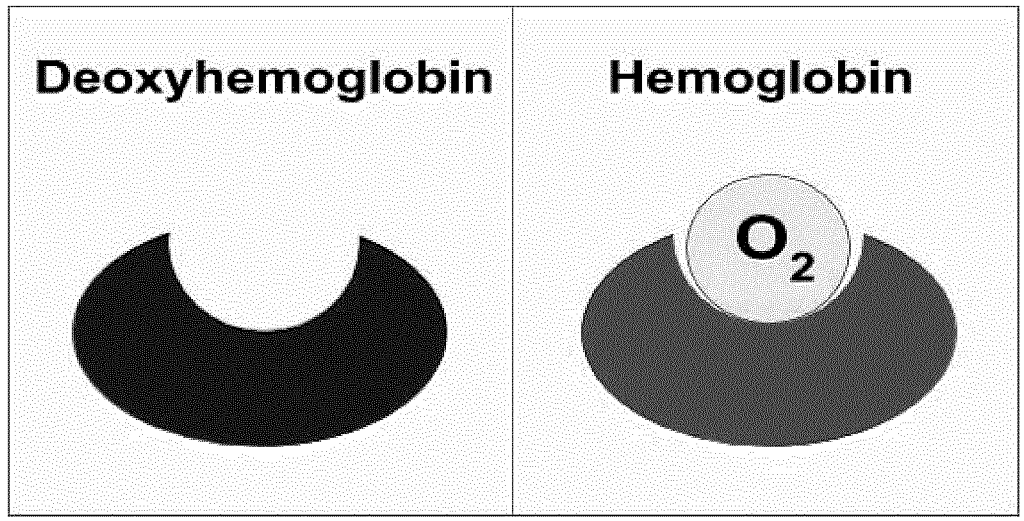
FIG. 14 is an example diagram of oxygen unaffixed and affixed to hemoglobin.

Pulse Oximetry: Transmitted pulse oximetry projects green light onto a person's skin, and analyzing the light reflected from the user's blood. The light from a green LED is emitted and then absorbed or reflected by the blood into a photodetector. The data collected by this photodetector can be analyzed to determine the user's heart rate and blood oxygen levels. When oxygen is affixiated to hemoglobin the pigment of the blood changes, as disclosed in FIG. 14.

Figure 15:
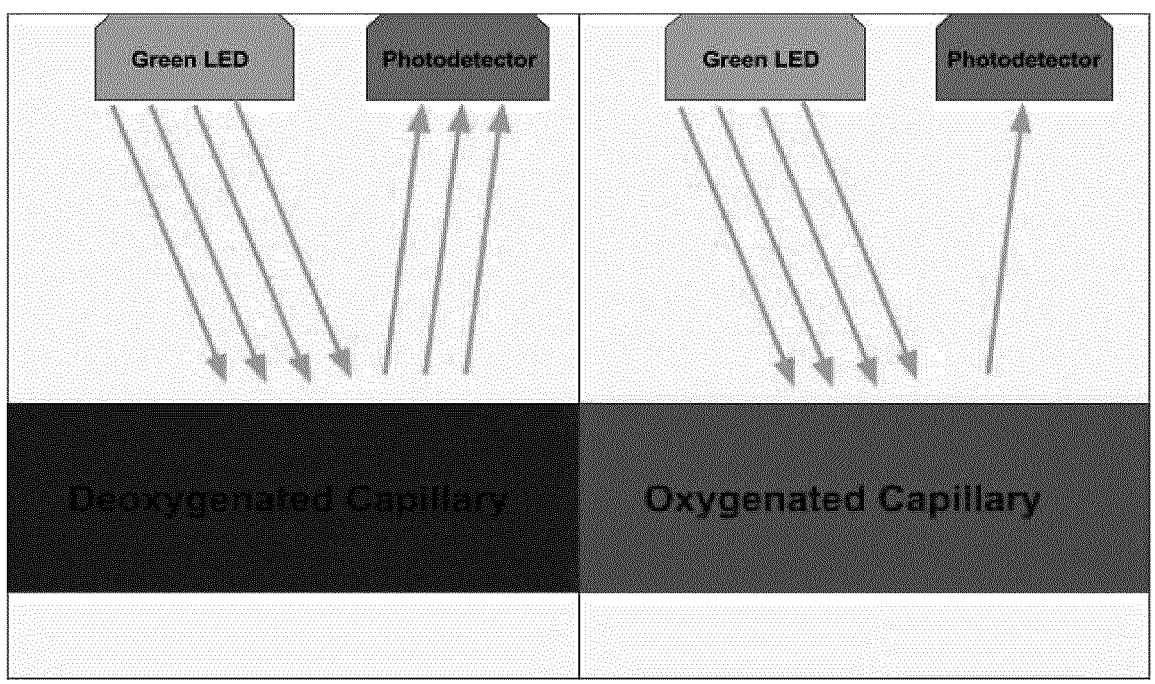
FIG. 15 is an example diagram of the relative oxygenation of blood, which varies the quantity of light received by the photodetector, which allows the detector to determine blood oxygen saturation.

With reference to FIG. 15, blue objects and red objects absorb light differently, which allows pulse oximetry to attain blood oxygen saturation. The relative oxygenation of blood varies the quantity of light received by the photodetector, and thus the detector can determine blood oxygen saturation.

Figure 16:
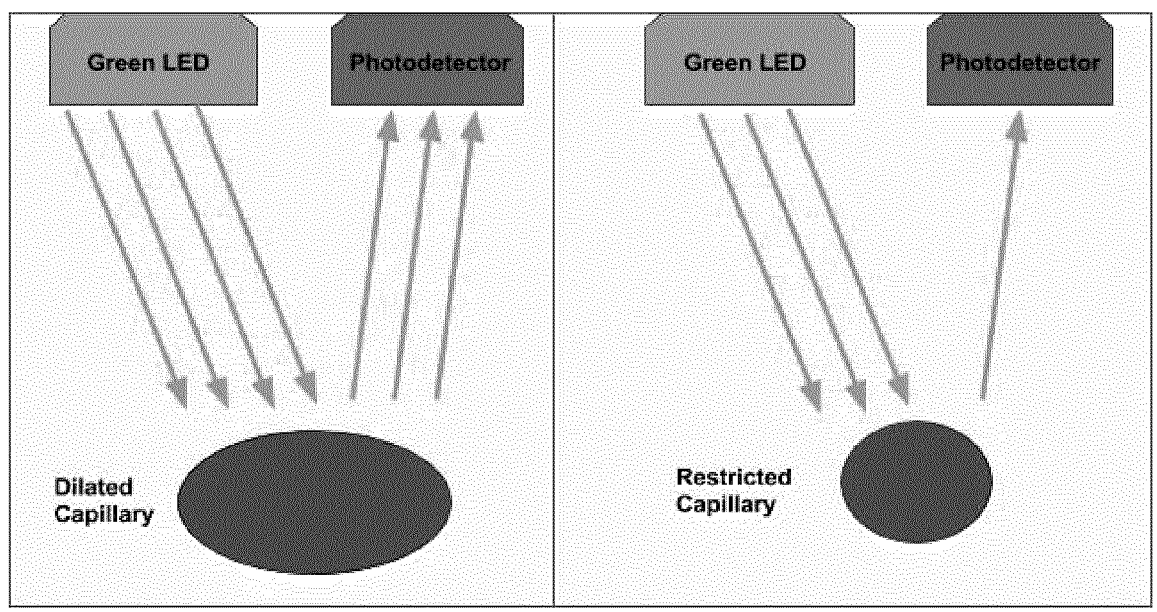
FIG. 16 is an example diagram that discloses variations in the quantity of light returned to the photodetector as the user's capillaries retract and dilate.

Pulse oximetry can also determine a user's heart rate due to variations in the quantity of light returned to the photodetector as the user's capillaries retract and dilate. This is disclosed in FIG. 16.

Electrocardiographs: The heart is a biological electrical system, using electrical signals, triggering the muscular contractions, which circulate blood. An electrocardiogram (ECG) is a biometric data set produced by analyzing the variations and movement of electrical signals in the heart. The electrocardiogram produces a waveform, which can be analyzed to determine cardiovascular irregularity. A normal waveform is disclosed in FIG. 17. A diagram of irregular waveforms, such as in a patient with heart rhythm disorder, can be seen in FIG. 18. An example diagram of a waveform of a patient with atrial fibrillation is disclosed in FIG. 19, and a patient with premature ventricular contraction can be seen in FIG. 20.

Figure 17:
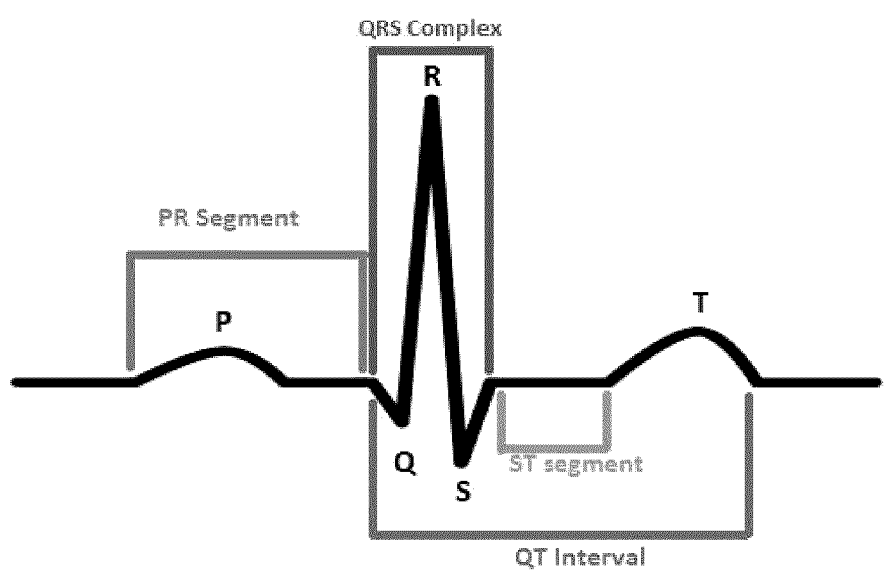
FIG. 17 is an example electrocardiogram produced by analyzing the variations and movement of electrical signals in the heart.

With further reference to FIG. 17, a single normal ECG waveform is disclosed. The P wave demonstrates the atrial excitation of the heart, the QRS complex demonstrates ventral excitation and recovery respectively, and the T wave demonstrates ventricle recovery. The PR and QT intervals act as a measure of time.

Figure 18:
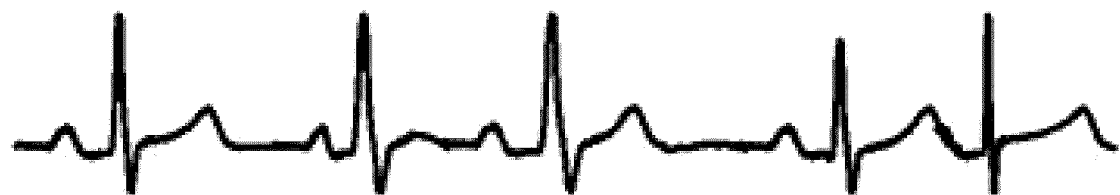
FIG. 18 is an example diagram of an irregular waveforms, for example as seen in a patient with a heart rhythm disorder.

With reference to FIG. 18, an ECG of a patient with heart rhythm disorder, seen in the aperiodic ECG waveforms is disclosed.

Figure 19:
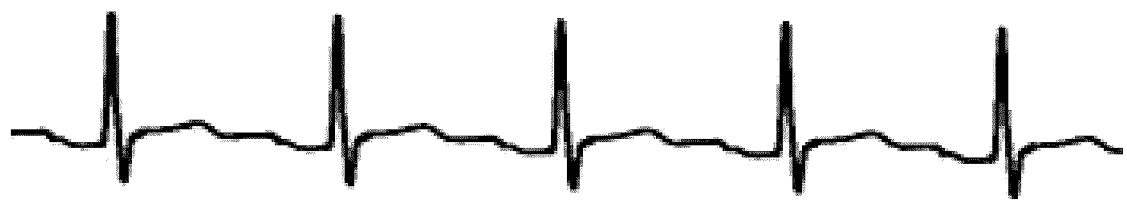
FIG. 19 is an example diagram of a waveform of a patient with atrial fibrillation.

With reference to FIG. 19, an ECG of a patient with atrial fibrillation is disclosed, seen in the missing P waves caused by a synchronized excitation of atrial cardiac cells.

Figure 20:
FIG. 20 is an example diagram of a waveform of a patient with premature ventricular contraction.

With reference to FIG. 20, an ECG of a patient with premature ventricular contraction is disclosed, seen in the sudden broad change in QRS complex shape.

Wet and Dry Electrodes for Electrocardiogram Acquisition: An electrode is a conductor through which electrical currents may enter and leave. A standard ECG is obtained through a 12-lead, ten electrode system, where a series of silver chloride electrodes pick up the small electrical currents produced in the cardiovascular system. Multiple electrodes are utilized in order to create a differential between electrical currents measured, in order to attain more accurate, through data sets. The positioning of electrodes to attain a typical ECG is seen in FIG. 5. These electrodes come in two variations, wet electrodes and dry electrodes. Wet electrodes are most commonly utilized in the medical system, as the electrodes are coated with a conductive gel, which increases the quality of electrical transfer between the body and the electrode. However wet electrodes must be replaced multiple times a day, and the usage of the conductive gel results in patient irritation. Dry electrodes on the other hand do not utilize conductive gel. This inherently makes dry electrodes reusable, without irritation, but also increased the level of electrode impedance, lowering the quality of data acquired if the system is not optimized for minimum noise.

Figure 21:
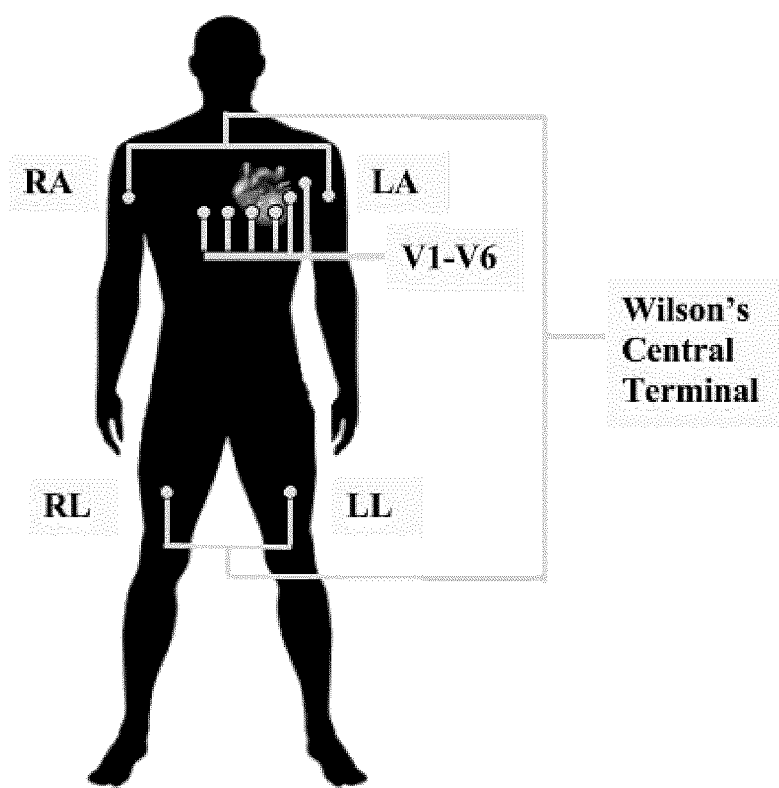
FIG. 21 is an image of an example electrode positioning of a twelve electrode ECG.

With reference to FIG. 21, a typical example electrode positioning of a 12 electrode ECG is disclosed.

A: Key Concept Explanations and Hardware Filtering Types

In the case of example embodiments of the system there is provided a hardware based filter. The system itself may not sustain full unfiltered data while still doing the same processing and keep up with other tasks. There are three main kinds of hardware based filter: Low pass filter, High pass filter, and Notch Filter.

Low Pass and High pass Filters

In example embodiments, low pass filters filter any kind of frequency higher than a cutoff frequency and only allow lower frequencies to pass through. High pass filters filter any kind of frequency lower than the cutoff frequency and allowing only frequencies higher than the cutoff.

Broadband Filter

A combination of a high pass and low pass filter creates a broadband filter. Through the concept of one filtering frequencies lower than the cutoff and higher than the cutoff means that only a set spectrum of frequencies can pass. The band is set by the cutoff frequencies of the high and low pass filter which is based off of the combinations of resistors and capacitors.

Electrical Impedance

Impedance is the opposition of current in a circuit when a voltage is applied. This is similar to resistance in a DC circuit, but impedance extends resistance into AC circuits where resistance in ac circuits or impedance has both a magnitude and phase. This is a perfect case of an ac circuit since the electrical signal of an ECG is always changing and alternating.

Smartwatches and the Pebble™ Smartwatch

Smartwatches are a compact technical system that is built to be equivalent to be a smaller phone on the user's wrist. Smartwatches are extensions on smartphones to make tasks simpler to perform without the need of pulling out a smartphone to perform that same task. Some examples of smart watches are the Fitbit™, Apple™ watch, Pebble™ watch, and the Samsung™ watch. The Pebble™ watch is a smartwatch that slows itself to have maximum flexibility meaning that the user can connect it to any kind of phone and with the special feature of adding specialty hardware to the watch. The Pebble™ watch also allows for their code to be open source so programming and extending the app is much easier compared to the other smartwatches.

B: ECG Designs

To make a wrist ECG viable creating a custom circuit board that minimizes noise, anti aliases the incoming data, and minimizes skin impedance is needed. Alleviating strain on the main processor, and optimizing the design for minimal surface area allows for a small and efficient wearable system.

Printed Circuit Board First Example Embodiment

Figure 22:
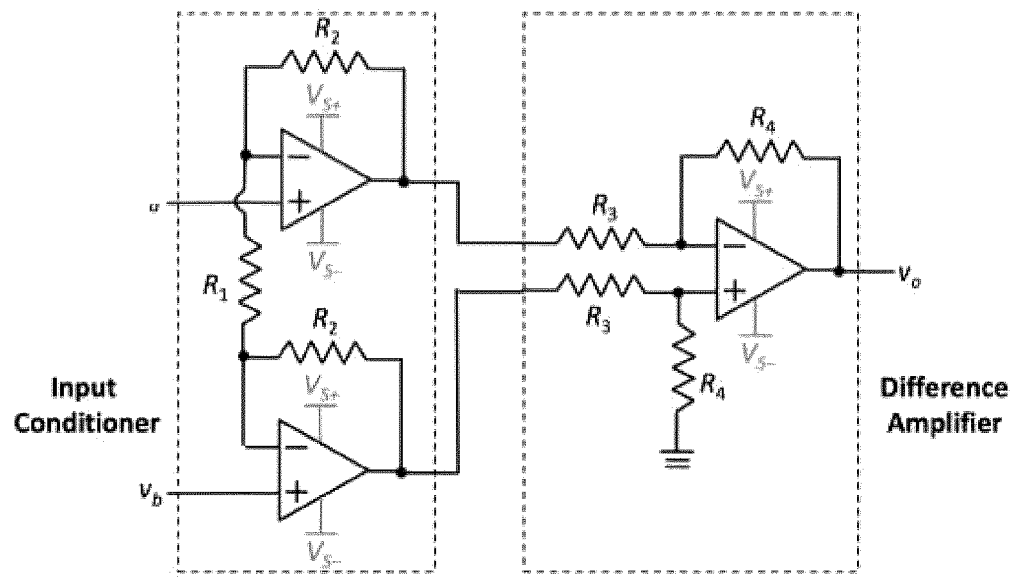
FIG. 22 is an example circuit diagram of an ECG data recorder.

In some examples, an ECG data recorder design was modeled similarly to FIG. 22 and constructed from off the shelf components. The input stage implemented an RC filter or PI filter, before the data was lead into an instrumental amplifier, with a right leg driver as common ground. The instrumental amplifier stage utilized, a 60 Hz notch filter, a high pass filter and a low pass filter, before the data was transferred to the gain stage. A final 60 hz filter filtered the data one final time before it was inputted into the system's MCU. Following this stage includes a cascading amplifiers op amp to adjust signal strength. This initial ECG design was an analog system with an analog to digital converter within its MCU. Unpredictable interactions between the system's multiple components, technically restrained this example embodiment. This primary ECG example embodiment was both too large and noise influenced to be effective. Running wires over a long distance without protection increases noise, thus this designs usage of components that do not take size or shape into consideration, increased the devices overall noise.

FIG. 22 discloses a simplified diagram of an electrocardiograph schematic. An ECG works with three stages an input amplification stage, differential amplifier stage, and a gain stage, with filters throughout the stages.

ADS1298 Component Breakdown

Further example embodiments of the circuit board revolved around the idea of cost effectiveness, ease of implementation and noise reduction, without oversimplifying the data obtained. The ADS1298 integrated circuit (IC) was the ECG sensor component, which was the focus example embodiments of the circuit board. The system's flexibility and capability to receive up to 8 channels of data from a maximum of 12 different electrodes, made the component ideal. The component also allowed for a Wilson Central Terminal (WCT), flexible programming, a small form factor, a right leg amplifier and the high resolution and low noise medical front end ECG needed to optimize the system. The WCT averaged the voltage of the three common ground leads from the ECG, to make the common ground for the ADS1298. The ADS1298 being a 24 bit analog to digital converter allowed for a possible $(2^{24}-1)$ different values for each channel input. This wide range of data allows the ADS1298 to collect higher quality, more precise data than other ECG ICs on the market. A Serial Peripheral Interface (SPI) bus acted as the communication method implemented in the IC, allowing the gain of the system to be fully programmable as well. The analog to digital converter on the IC reduced strain to the MCU, while remaining high resolution.

ADS1298 Printed Circuit Board Example Embodiments

The optimized circuit board for the ADS1298 was broken down into four example embodiments. Example embodiment one was made to take advantage of the WCT. Example embodiment two shared this same functionality, but by having unset capacitors and resistors, allowed for more flexibility. The third example embodiment aimed to take advantage of the right leg filter more than the WCT, to allow for more flexibility in the number of electrodes used. The next revision aimed to minimize noise by implementing low dropout voltage regulators, logic converters, and minimum sized components. The third example embodiment reduced the circuit board size from 30 mm by 50 mm to 17 mm by 30 mm. The fourth example embodiment of the circuit board was optimized to reduce noise even further on a smaller sized board, whilst making a flexible and compact system. The ideal behind a fifth example embodiment of the board was used to make three final boards. The first still capitalized on the WCT feature of the ADS1298, the third board was designed as a breakout board to allow for the most testing variation and finally a fifth example embodiment of the board was designed to take advantage of the right leg driver. These final board designs had high noise reduction, a smaller size, yet could still provide the reliable and flexible system that was required. Using smaller footprint capacitors and resistors reduced distance between the IC and the capacitors reducing the chance of a feedback loop. The low dropout voltage regulator kept the voltage from the IC as constant as possible to reduce noise caused by small ripples in the voltage. Lastly all further example embodiments implemented ground and power pours. The purpose of the pours was to allow the power rails of the circuit board to be used instead of small traces. The WCT variations seem to be the most efficient, as they allow for a lower number of electrodes on the device, minimizing the devices cost and size. The 3D models of all of the relevant printed circuit board example embodiments are seen in FIGS. 23, 24, 25 and 26.

Figure 23:
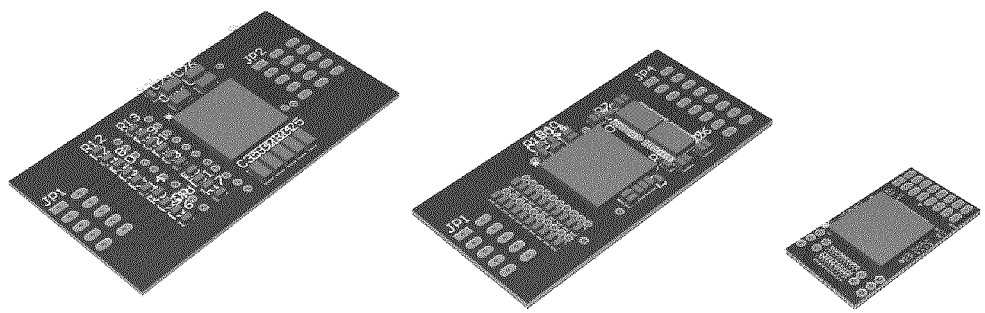
FIG. 23 discloses an example 3D model of an example embodiment of a printed circuit board that takes advantage of the Wilson Central Terminal with surge protection on board to ensure the safety of the board.

FIG. 23 discloses an example 3D model of a first example embodiment printed circuit board. This version of the printed circuit board takes advantage of the Wilson Central Terminal (WCT) with surge protection on board to ensure the safety of the board.

Figure 24:
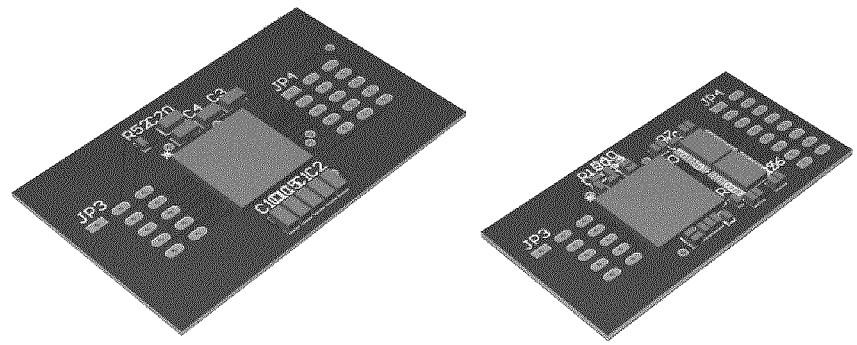
FIG. 24 discloses an example 3D model of a further example embodiment of a printed circuit board that takes advantage of the Wilson Central Terminal and leaves full flexibility for the kind of protection and filtering for the electrodes FIG. 25 discloses a further example 3D model of a third example embodiment of a printed circuit board that does not take advantage of any kind of specific feature of the integrated circuit, and allows for the full flexibility of the integrated circuit.

FIG. 24 discloses an example 3D model of a further example embodiment of a printed circuit board. This version of the printed circuit board takes advantage of the Wilson Central Terminal and leaves full flexibility for the kind of protection and filtering for the electrodes.

Figure 25:
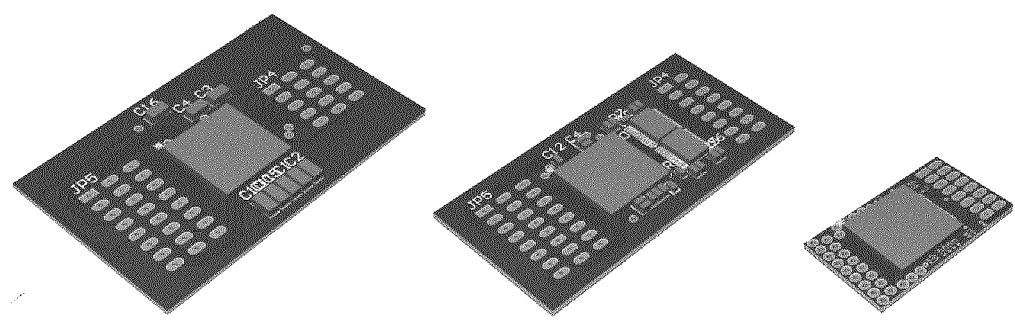

FIG. 25 discloses a further example 3D model of a third example embodiment of a printed circuit board. This version of the printed circuit board does not take advantage of any kind of specific feature of the integrated circuit. The board allows for the full flexibility of the integrated circuit.

Figure 26:
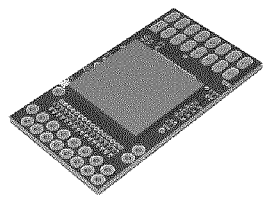
FIG. 26 discloses a further example 3D model of a printed circuit board with a level of surge protection and hardware filtering done on the board itself.
Figure 27:
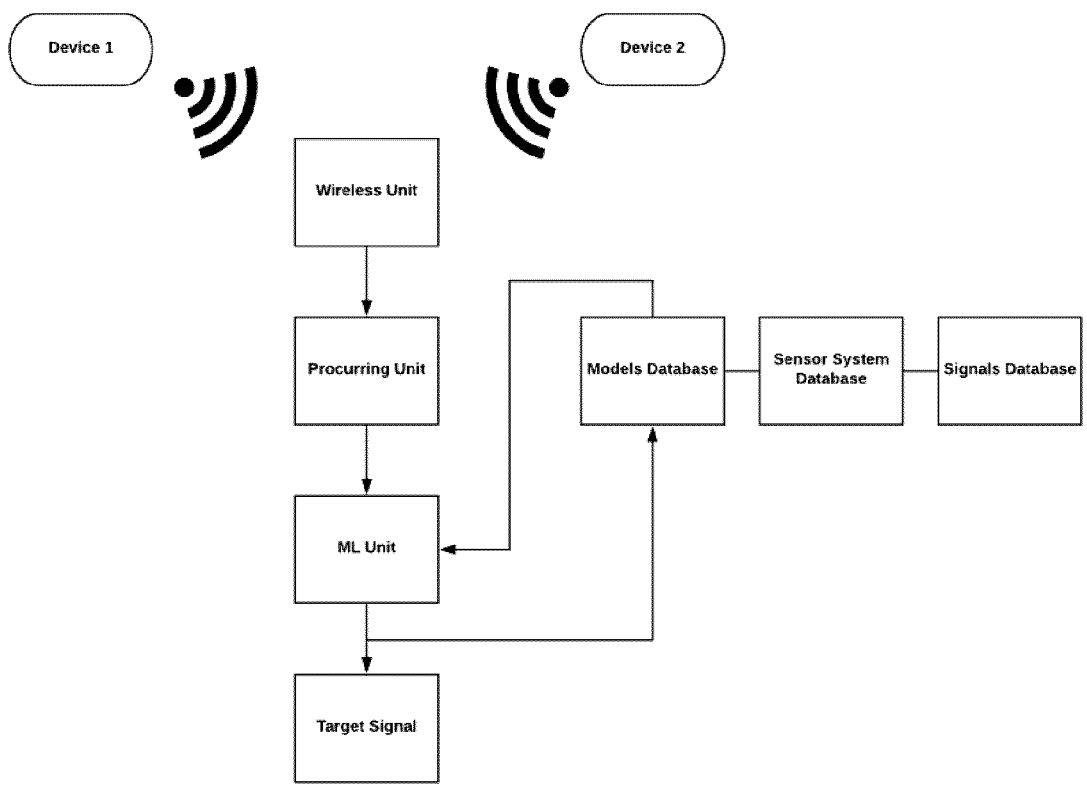
FIG. 27 is an example block diagram of two devices communicating with a wireless unit.

FIG. 26 discloses a further example 3D model of a printed circuit board. Similar to the example embodiment of the printed circuit board disclosed in FIG. 25, there is some level of surge protection and hardware filtering done on the board itself.

C: Software Algorithms and Filters

Fast Fourier Transform (FFT)

The Fast Fourier Transform is an algorithm commonly used to filter out noise, and to easily analyze the data. The transform is commonly used for its light way and easy implementation. In example embodiments, this transform may play a critical role in helping to remove lower level noise that could not be filtered out using the hardware.

Cross Correlation

A cross correlation algorithm is an type of algorithm that is used to determine similarity of a dataset or a waveform to another waveform. In example embodiments, this is one of the most critical algorithms in the system. This must be used to help determine if the user has a normal heart rhythm or a rhythm that indicates a patient is in a critically dangerous situation.

Autoregressive Model

The autoregressive model is an algorithm commonly used to remove outstanding data, or outliers. This algorithm will play a critical role in helping to smooth out the data to better cross correlate the data. Having outliers in the data set will cause for incorrect cross correlation. The algorithm smooths out the data set by using the previous pieces of data to help determine if the next piece of data is an outlier or not.

Finite Impulse Response (FIR) and Infinite Impulse Response (IIR) Algorithm

In some examples, both filters serve a purpose of amplifying a desired frequency and attenuation all undesired frequencies. Both filters cannot be applied at the same time, it is one or the other. The IIR filter is very lightweight and easy to implement, but has stability issues. The FIR is much more computationally intensive, but has far less issues.

Example Data that Would Determine a Distress Situation

In some examples, mainly ECG information is used for a stronger indication of overall health. Pulse Oximetry is not used in some example embodiments. Movement data may be used as a reference against bad looking data to check the bad data is due to movement noise. Pulse oximetry data may be used in some examples as an extra dataset under the doctor's discretion to add confidence in the system decisions. Further, other sensor data sets may be used.

Error Checking Specifications

Key point: It is important to note that the system understands there exists a greater importance in preventing false negatives (missing an regular event) then having a false positive (detecting an irregular on healthy data) Thus, in example embodiments, the system is modelled around preventing false negatives and is more lenient on having false positives. It is better to overcompensate then to not get help for the user.

For Emergency Situations

Example embodiments related to system Error Catching:

1. First line of system error catching is catching multiple/consecutive events;

2. Second line of system error catching is to compare the collected data against the user's baseline healthy;

3. Third line of system error catching is to check data against movement data;

4. Fourth line of system error checking is to check collected data against a set database on system of known heart irregularities;

5. Fifth line of system error checking is sending the data out to a more computationally advanced systems (one of which is not feasible on a wearable device);

6. Sixth line of system error checking is obtaining the user's input, and/or question the user;

a. There are many methods for checking user response methods such as response to question b. Time to response c. Ability to respond First line: A case representing serious cardiac events would only call for medical attention if multiple irregular heart beats occur over a period. That means that we are not looking for just one off beat, but rather many over a short time span and which a high frequency.

Second line: The system's goal is to detect an unusual event. An unusual event is classified as an event that differs from the user's typical baseline data. The system checks against the user's current normalities to ensure nothing is in the normal.

Third line: Movement is a large contributor to noise resulting in bad data. Checking against the movement data will help to rule out any potential detection of error due to movement.

Fourth line: To avoid errors (or false event detections), checking against normalities in the system (and other pieces of data preloaded onto the system) is required.

Fifth line: Running data through an external more computation system is critical to help identify what kind of event is occurring in the user. This also supports in identifying what kind of event this is.

Sixth Line: The final example line of error checking is to check against the user themselves and see the feedback given to the system. Different questions for different cases (or no responses) can mean different things. Having the device make recommendations would change the level of claims of the device.

Handling of Error

The following discloses example core requirements of the system when a piece of data is determined to be error data:
 Save the piece of data as error data
 Hand off the data to head server
 Mark the data on system as error data
 Mark data with reason for error data
 System excludes the data from processing The importance of collecting error data comes in to better help the system identify an error the next time around.

Priority of notification is set by the user and the user will determine who it will go to:
 Under Emergency Situation:
 1.EMS
 2.Family under setting
 3.Close neighbour if set to notify, or other contacts
 4. Notification sent to patient file for issuing doctor
 Under Abnormal Event:
 1. Notification sent to family
 2. Notification sent to patient file for issuing doctor
 Under Emergency Event with a User Override, in Other Words, the User has Overridden the Emergency Response of the System:
 1.Family will be notified
 2.Notification will be sent to issuing doctor
Under Forced Distress Event
 1.EMS
 2.Family members In some examples, all potential notifications are first acknowledged by the user before being sent.

Human Body Communication (HBC)

This methodology uses the human body as a arrangement of biological resistors and capacitors to create a circuit system and channel of communication. In sending and receiving signal from difficult locations around the body, strong communication pathways can be formed and used to carry out many functions. The human body in this methodology mimics a wire.

Using high frequency signals in the body and transmitting it throughout the body to produce a baseline by understanding how signal potentials vary in phase and amplitude through different biological features.

A core function of HBC is to construct a common reference factor between multiple sensor placed around the body. This is achieved by transmitting a known signal amongst the devices through the human body. In understanding the phase and amplitude distortion that occur through the body a accurate prediction of the received signal can be constructed. In comparing this predicted received signal to the actual received signal a correction factor can be applied to future collected signals to reduce potential float of reference voltages.

A parallel core function of HBC is to provide accurate time syncing of sensor devices around the human body. This is achieved by sending a known signal among the devices at a specific time. Knowing the sent signal and expected time delay that would occur between interfacing devices can be compared to the collected signal to compensate for any misalignment in device clocks. The two key characteristics that must be monitored in HBC is the time of all network devices to produce a consistent time among all collected signals' time axis and secondly to see how the body distorts a signal over time.

Modulation (or fixation) of both amplitude and frequency is needed to correctly monitor the change of a signal as it propagates through the body. All signals are recorded on the device and analyzed on software to produce the working signal. The core feature described is used to then time sync devices and/or develop a correction factor in a reference voltage. This is complete through means of software signal manipulation.

Using the body of the wire will reduce the variance in time lag (as well as delay) and increase the time synchronization with the devices to allow for better correlation and increase accuracy. This is due to the fact that the body is used as an electrical wire. This is highly important as the synchronization time can affect the level of common mode rejection and proper differentiation of the signal itself.

The device producing the signal will be injecting a signal into the human body with low current at a frequency in the 1 to 100 megahertz range. In this range, there is less of a possibility of confusing the signal with other environmental noise, such as high EMI noise or lower frequency body noise. Higher frequency signals are chosen as they can pass through the body with more ease. This is to prevent misidentifying any natural noise coming from the human body with the injected signal. The higher the frequency of the signal, the better since it will allow for a better understanding of how quickly the variance in potential float is occurring. For the device that is collecting the data, the device needs to sample at least 2× to 5× the frequency of the signal to determine variance. A highly unique signal composed of multiple features is used to further distinguish the transmitted signal from environmental occur signals.

Different levels of filters will need to be implemented then a classical ECG both on hardware and software to ensure that all signal fidelity is retained to produce the correct compensation factor. In addition a recurring calibration of wireless devices will further improve the accuracy of the results.

The compensation factor from the collected signal is determined through different metrics measured based on the collected signals such as changes in the phase and gain.

B) Gain Phase Analysis

Using the analysis of phase and gain shift of signals sent through the human body is a clear indication of the body's chemical physiology. The process works to understand the bioimpedance of various body structures to predict how potential and signals vary as they pass through the body. The information gathered from this technique is used to construct a circuit models of capacitors, inductors, and resistors that represent the body. Understanding the changes and covariance in these factors can support in helping in creating the compensation factor for software to produce the target signal.

The method works by transmitting and receiving varying signals in gain and phase through localized areas around the body. In comparing the transmitted and received signals and the changes that exist, a model of the bioimpedance of the localized area can be constructed. A potential example of the this setup is transmitting a signal from the right bicep and receiving it on the right tricep. The signal can be compared to extract information on the complete gain and phase changes as it passes through the arm. This information can be related to a bioimpedance value. Repeating this process throughout areas of interest on the body can be superimposed together to construct a complete body bioimpedance model. Allowing for a better compensation into the adjustment factor for the target signal Biasing Using hardware to create a localized bias on the body to control its potential to a normalized and consistent to a reference point. Implementing a central device to output a specific DC potential will force the body (or the parts of the body where the devices are at) to vary around a known a consistent voltage. In some examples all devices utilize the body biased potential as their reference ground, thus establishing a point of comparison. This technique eliminates the impact of the battery ground floating due to EMI. However, such a fabricated bias is influenced greatly by the human body's resistive and capacitive features. Thus, a reliably consistent area of the body with minimal bioimpedance variances is chosen as an area of interest in order to accurately predict the human body effects on a DC bias voltage.

The implementation of biasing can come in different forms—in this form the sensor technology will be driving the bias to produce a comparable reference voltage for signal comparison. The implementation of the biasing technology works by having each device on the body contribute to the part of the bias to the body. Once the system agrees upon a bias, a central module will be communicated via a signal sent throughout the body. At this point all wireless device know what the agreed upon bias is and emulate the bias locally. This eliminates the distance a bias must travel between a biasing system and a sensing electrode. In doing so, each device will receive a biased signal that is less influenced by both EMI noise and gain and phase distortion from the body. What this creates is an agreed upon reference voltage as a basis for proper comparison.

A hardware system will generate a consistent DC signal, which will be passed through multiple current and voltage limiting circuit blocks into a transmitting electrode. This electrode will act as the interface between the biasing system and the body to transmit the signal. Remote devices will detect features of the signal to ensure the system is correctly biasing each localized area.

Right Leg Drive (RLD) Systems

Reinjection of noise back into the body as a negative feedback is used to reduce the noise in the signal for an increase in data fidelity.

The methodology of biasing and RLD are really similar. The RLD approach varies by implementing a bias voltage back into the body. This voltage is sent into the body as a negative feedback to achieve a common mode rejection system, thus decreasing the common mode voltage noise gathered from the sensors.

For a system like the RLD to work it uses a localized bias where there is a distinct common mode. What the circuit does in this case is push the noise floor down on a more localized level directly where each sensor location is found. This means that at the location of data collection there will be a signal with the distinct target signal with lower level noise or baseline shift noise due to potential variance. With the RLD the system can collect both the target signal and a noisy signal which will contain the common noise between the two. These signals will be averaged and reinjected back into the body to reduce the common mode, thus reducing the variance at that localized level. In doing so, this will reduce the ground variance when differentiation the ECG signal on software for all sensing locations.

This can be performed using a negative feedback circuit (negative feedback loop). This is implemented at a localized level, beginning specifically at the location of the sensor. The common mode noise gathered from multiple sensors located around the body is determined through a hardware/wireless software means. This common mode noise is then inverted, amplified and transmitted back into the body to deconstructively cancel out and eliminate the common mode noise. The common signal is influenced by the sensor placement. The sensor placement is chosen as to not remove any aspect of the targeted signal by prior analysis of various areas of interest.

Similar to biasing the body, a hardware system will generate a consistent "common mode cancellation" signal, which will be passed through multiple current and voltage limiting circuit blocks into a transmitting electrode. This electrode will act as the interface between the biasing system and the body to transmit the signal. Remotes devices will detect features of the signal to ensure the system is correctly biasing each localized area.

ML Software

ML (machine learning) is used to compensate for the fluctuation in ground via good and bad datasets. Understanding the function that governs the floating ground between the wireless nodes allows for a correction to be applied to the wireless signal collected. This includes using weighted values to emphasize on certain values and datasets in order to mitigate the float between devices.

Good datasets can be made by employing a forced common ground using wires and hardware to make training data initially. The application of this solution will require a larger pool of data for it to be able to identify and remove the target signal High Order Filter The underlying contributor to the reference ground float is due to electromagnetic interference (EMI). Due to each wireless device being located at different places around the body, each one is susceptible to a different total EMI. This leads to the reference ground float between multiple sensor in unpredictable ways. The implementation of higher order filters can remove intrinsic high and lower signals caused by EMI and other undesired signals to drive down the noise floor. This may reduce the impact of EMI and the overall reference ground float.

In a similar manner to a higher order hardware filter, a higher order software filter will also used. Using software as a method of further increasing impact of filtering. In addition software is able to compensate for signal distortion that may occur due to the higher order hardware filtering. A software filter has the benefit of employing a variable filter and amplification scheme dependant on the current status of the signal.

Modelling Human Body on Software

The software uses different models of the human body to anticipate how fluctuations and changes in the potential in the human body will occur. In doing so the software is capable of predicting how various devices will float as electrical signals pass through the body. These floats are compensated for in producing a wireless ECG. Some models will allow for us to understand larger spikes of noise if that is noise coming from other body parts or inherit random noise.

Both filtering system will filter out data in specific frequency ranges of interest. One in particular (but not the only one) is the range of 0.05 Hz to 45 Hz as used in common ECG monitoring devices.

EMI Shielding

Using EMI shielding around the device and sensor technology to reduce the amount EMI pick up. In doing this, less baseline shift occurs at the different locations which in turn increases the accuracy of the collected signal. Various methods to achieve this includes but is not limited to implementing copper framing and enclosures, utilizing EMI resistant electronic components, implementing an active shielding hardware system that actively measure EMI to emit it through a negative feedback system to eliminate it. This method has the benefit of a reduction of influence that EMI has on the system and allows for a greater focus on internal noise in the body.

Implementation of above methods

The combination of all potential solution of various magnitudes will work in conjunction to extract the strongest wireless ECG signal. Higher order filtering on the hardware and software can strongly anneutate noise of high and low frequency EMI. In doing so, the baseline float is reduced to a larger degree. Capacitive sensors work ideally in a certain frequency range and have a worse performance as they reach very low frequency signals and DC signals. This fact can be exploited to understand that any signal outside frequency of operation can be deemed noise and removed from the signal. We would need to implement higher order filtering on software and iteratively run the signal through the software many times to push the noise floor on the signal down as much as possible. Once the noise floor is reduced as much as possible we move into using model of the human body. We would be using and calibrating different models of the human body:

Electrical characteristics of the body in resistors, capacitors and inductors
   Blood vessels locations, arteries and capillary action
   Mechanical Characteristics:
   Liquid mechanics of blood
   Mechanical anatomy of the body size and shape
   Chemical Compositions
   Bone characteristics
   Chemical property of the body
   Weight and Height models
   Bioimpedance variance within the body and relative phase and reactivity models
   Other electrical models of the body, including signals from the brain, nerve endings Example embodiments can use different combinations of human body models to support in extracting the target ECG signal. The goals is to understand the variance of electrical signal that occur in the body. We would reduce the outside EMI noise and noise floor from the environment using filtering. Next we use models to support in algorithms and Machine learning system to find the correct weighting of models and pattern recognition to find the target ECG signal. We would first train the network using high fidelity data sets to teach the system the features of a high fidelity dataset. While adjusting the weight factor of different electrical signal models from the body, the network has the ability to extract features of the target ECG signal and discard undesirable features of the signal that correlated to other bodily systems.

The implementation of EMI shielding is really core for reduction of environmental EMI and sudden changes in the external environment. Implementation of shielding is core for stabilizing the signal from the capacitive sensor to reduce the scope of its signal detection. The second need for implementation of EMI shielding is to reduce the noise going into the analog front end.

Reduction of Potential Variance Noise Through Array of Sensors

Using an array of sensors at specified location for the purpose of collecting undesirable signals such as (but limited to) muscle noise to further understand the spatial and temporal noise signal. The attenuation and change in phase a signal experiences as it passes through the body can depict where and what the signal is. By employing multiple sensors around the area of interest, a strong understand of the initial signal can be collected. This understanding can be utilized to remove signals that are not the targeted signals to compensate for it on software (and DSP processing) to achieve the target signals (and noise). This is used to classify noise to produce a model that can amplify the targeted signal.

The function of an array of sensor is the reduction of noise to get the target signal. When using the device the data from the same multiple array of sensor is sampled and fed into a processing unit. There can be a distinction between sensor that are ideal for collecting strong ECG signals and sensors that are ideal for collecting strong noise signal. There are locations with high noise or locations that has the target float in signal. These locations might yield different data such as EMG data that might superimpose on the ECG data. The implementation would work where the target locations are already known and have software system to confirm that data is coming off at the location. Then there is processing on the device to compensate on the target data stream the noise and potential baseline shift data. This method would take the target stream of data and use the noise stream of data and extract what is considered noise and superimpose parts of the target signal that have higher data fidelity at other sensor locations. This would use at minimum twice the amount of sensors available at each location, the more additional sensors the better for results.

A particular example is to reduce the muscle noise in a signal. Muscle signals are generated at a localized area on the body. As the signal travels away from this area, the signal is attenuated and altered in phase. Due to uncertainties of the body's impedance with only one sensor, limited information can be constructed on what the original signal is. With the addition of multiple sensor that vary in location, a strong depiction of the original signal can be construct. This increased accuracy in understand undesired signals can be removed from the target signal to increase data fidelity. This can be applied to all aspects of noise signals.

Example Sensor Technology

Figure 35:
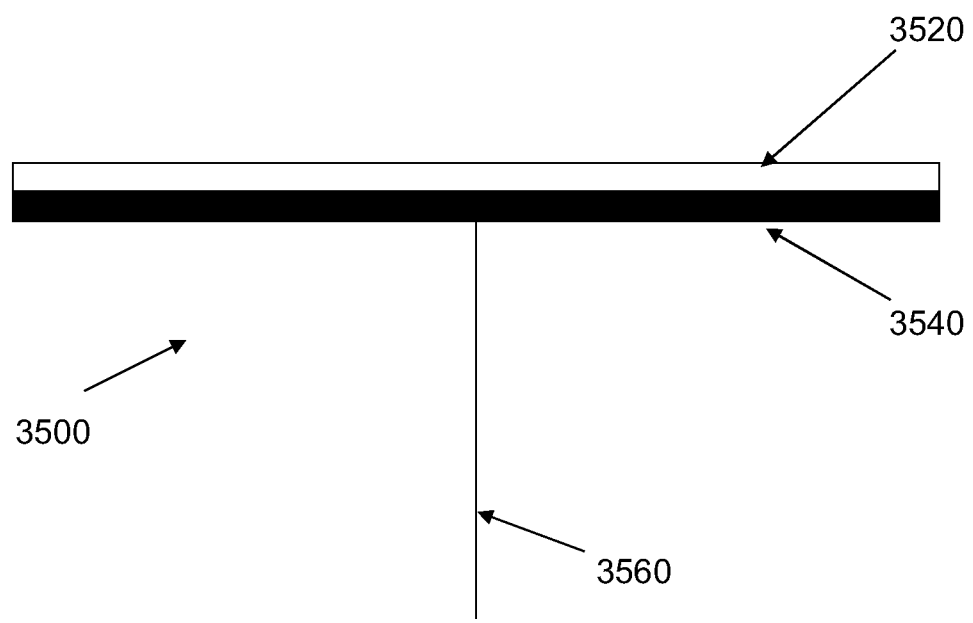
FIG. 35 is a block diagram of an example sensor.

With reference to FIG. 35, the example core sensor on the technology itself is a capacitive electrode 3500. The example capacitive electrode 3500 may include a top oxide layer 3520, and a bottom metal plate 3540 and an electrical wire 3560.

Now this is not restricted to only making the system work based on a capacitive sensor. Now depending on the implementation of sensors this leads into different preconditioning circuit setting. If you use a sensor with a low signal amplitude there needs to be a higher gain setting. The goal of any ECG sensor that is used and applied into the system is that it measure electrical reactivity in the body. The need for a capacitive sensor comes from the need to increase comfortability in the patient. The application of a capacitive sensor allow for a high data fidelity while allow for a patient comfort through the fact that there is no need for a wet adhesive.

This electrode is further complemented by having a complimentary circuit that has a few key components of negative feedback, bootstrapping, baseline compensation and amplification and gain settings.

Core important specifications is that the oxide layer needs to be a high dielectric constant substance that would create an High Impedance layer. The thinner the dielectric layer the better the capacitance effect.

The core features that make the sensor viable for application in the system is high Impedance and no need for wet adhesive. The whole application is that there already exists an insulator so it works by working similarly like an capacitive sensor. There are some setbacks with the sensor is that since there is no super firm contact there needs to be more work into fixating the sensor in a good location. There needs to be increased filtering since the sensor will be more susceptible to noise since it is more sensitive.

For mounting of the sensor technology itself, it depends on where the sensor will be placed, the sensor technology is made to be universal. There are only two core items to be careful about. That is to make sure the device is fixated in good position, there is good shielding of the sensor itself to increase data fidelity.

Some method of this can be seen in other products seen in the market is other capacitive sensors like the EPIC sensor or QUSAR sensor.

Grounding Problem

The reduction and solution can be achieved through several possible means of having a system to measure the potential variance and float of the human body and producing a compensation factor. The benefit of collecting ECg data is that it exist in a very short frequency range. What is allows for is there we can put higher order degree filters and filtering of noise that is not a contributor of the target signal. Reduction of the frequency range will make it easier for us to perform differentiation and achieve a target signal. There are other methods we would add onto this method to help us reduce noise and collect the target signal. Shielding for EMI, other noise reduction methods. Since noise can still exist in the target frequency range we would also be training and developing a model that can weight different parts of the dataset to optimize for target signal and subtract as much noise as possible in the target signal. Other methods of trying to reduce the floating potential is analysis of complete noise and target signal and subtracting the noise from the target signal. This is mainly achieved by using an array of sensors, so increasing the amount of sensors and finding both target signal and complete noise. This is a method for us to find the common mode and subtraction. Finally there are methods of biasing and producing a system of negative feedback to reduce the common mode voltage in the entire system. This can be further complimented by using a biasing method to achieve an agreement of baseline around the device. The mentioned solutions can be parts of the entire puzzle. EMI shielding can be implemented. Filtering degree can be implemented.

The cause for the grounding problem and variance is due to the fact that there is a variance with the battery potential and no agreed upon potential. The next is the continuously fluctuation of potential in the body. There is a factor where the device and body is also susceptible to EMI noise. There is an effect of EMI noise mainly to the arms and limbs of the body less so the core. This is due to the fact that the arms can act like an antenna for EMI noise. This can be seen when there is more noise in the T-P segment in just any kind of ECG data that is collected from the hands or arms.

Wireless Network of Sensors

The goal of the wireless network of sensors is to make an expandable system. One of the core features to make this possible is getting the clocking system to be synchronized amongst the device. This is achieved using the wireless network of device. This can be achieved using any kind of wireless protocol. Depending on the protocol itself to achieve as close to perfect synchronization there needs to be code as close to the metal as possible to reduce the lag from the software stack. This allows to us to achieve sub millisecond accuracy. This allows for us to achieve a network of sensory data since the accuracy of synchronization will allow us to properly correlate the data. This feature is also really key to making sure that there is proper differentiation of the device.

One of the core features of the having a wireless network of sensors is that it allows for expandability of the device to have multiple sensors and sensor locations. This ability allows for users to choose when and what sensors they want to use and the data they want to collect. This becomes highly important for patient comfortability for people to have the choice what sensors they want to place on.

Figure 36:
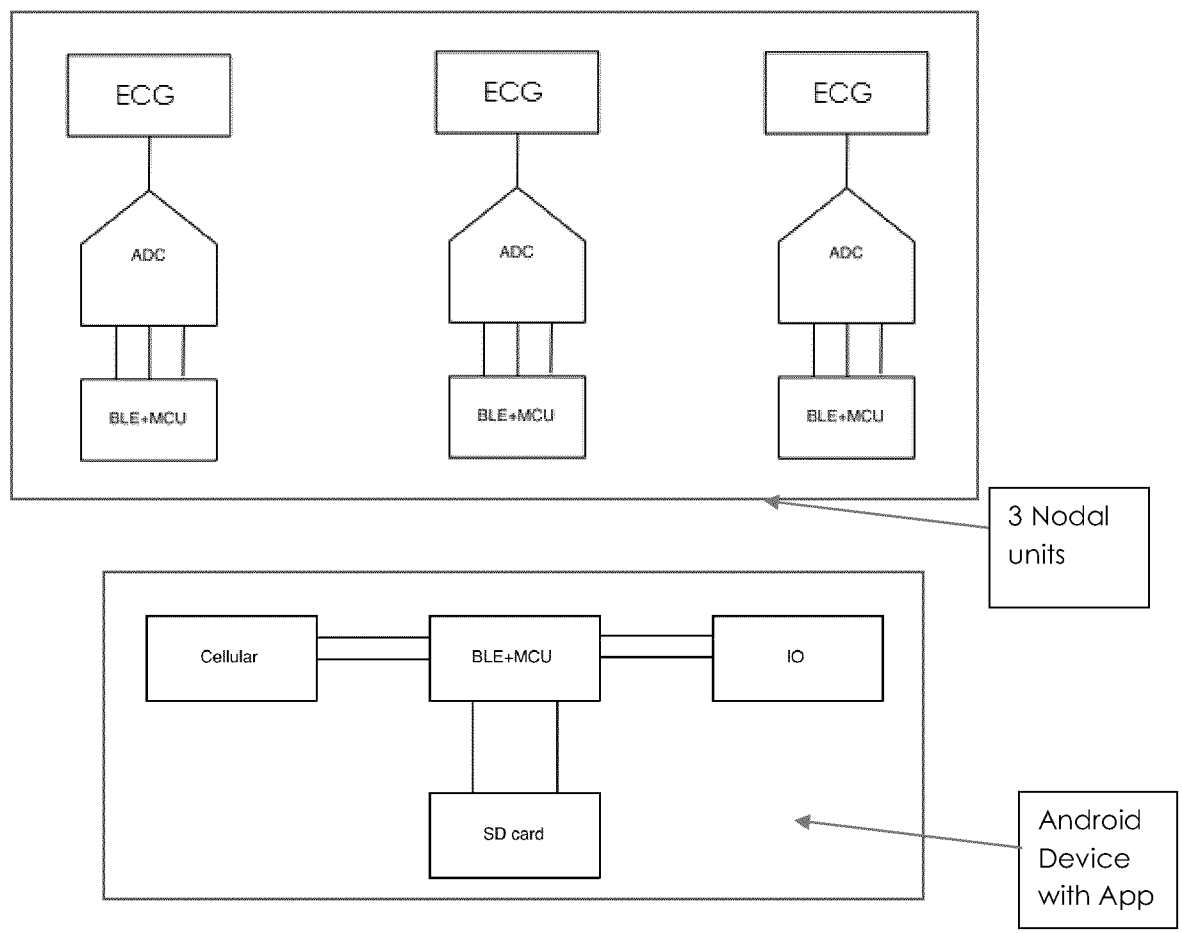
FIG. 36 is an example network diagram of an example system setup include three nodal units.
Figure 37:
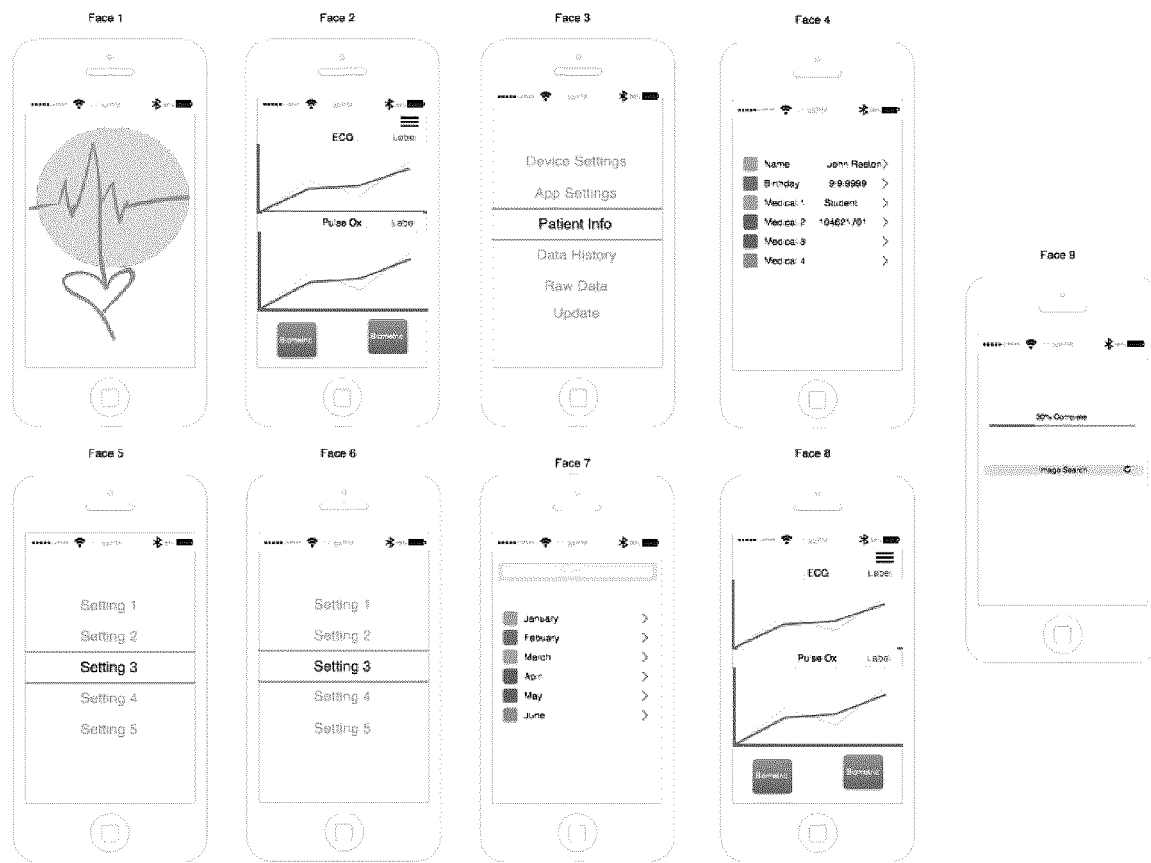
FIG. 37 are example screenshots of a graphical user interface.

With reference to FIG. 36, the most probable setup is having 3 identical devices that would each act as one electrode. For the receiving end there are a few core features that we would need it to perform and that performance can be replicated by a Smartphone or Android to drop on more things that would need to be developed. The main device where all data gets transmitted to can be developed in house or other device made compatible. The other option is we make one of the wrist units to be the main device. There is a lot of variation and possibility to make this happen. In the diagram, the 3 nodal units core important parts is the ECG sensor also the capacitive high impedance sensor, the ADC which is used to turn the ECG signal into a Digital signal that can be processed. Finally the MCU and wireless transmitter to do initial processing of the signal and then sending it to the main unit for differentiation. Any additional components are mainly features to make the device more usable for the patient.

TABLE 2

Table Requirements for lead definition

| Lead | formula | Name of lead |
|---|---|---|
| I | LA − RA (left arm − right arm) | Bipolar limb leads |

TABLE 2-continued

Table
Requirements for lead definition

| Lead | formula | Name of lead |
|---|---|---|
| II | LL − RA (left leg − right arm) | |
| III | LL − LA | Einthoven |
| $aV_R$ | RA − (LA + LL)/2 | |
| $aV_L$ | LA − (RA + LL)/2 | Augmented leads (Goldberger) |
| $aV_F$ | LL − (RA + LA)/2 | |
| $V_N, N \in |1 \ldots 6|$ ($V_N$ − chest lead) | $V_N$ − (RA + LA + LL)/3 | Unipolar chest leads (Wilson) |

Example Leads Calculation for 12 Lead ECG

Data Filtering and Processing

Filter for the data exist both on hardware and on software. an ECG signals exist in a range of 0.05 Hz to 100 Hz. Depending on location there is noise that exist at 50 or 60 Hz due to powerline noise. On hardware there needs to be ADC preconditioning so there is a low pass filter to act as aliasing in addition. The cutoff exist a 100 Hz at minimum. There is a notch filter to remove powerline noise. There does need to amplification to make sure that the signal is visible. On software there is baseline wander filters and low and high pass filter to remove additional noise. There is processing on firmware which is signal decimation/averaging at the point of collection.

Theory of Operation of a Capacitive Sensor

The theory of operation of a capacitive sensor is like that of a normal capacitor. The change in charge is measured by the capacitive sensor. Like a capacitor when charges of one plate separated by a dietetic changes in charge it is reflected upon the corresponding plate. In this case the human body has a fluctuation of charges due to ionic conduction which allows us to measure the ECG signal. An aspect of the capacitive sensor is that it has the ability to be reused because it is either a noncontact, by the fact that there is dielectric generation, or contact sensor, by the fact that it touches the person, that requires no adhesive, the signal coming from the system is amplified. Some of the benefit of capacitive sensors is that even though there would need to be a means of fixating the sensor it can be worn for longer periods of time. It can be reused many more times. There is no irritation since there is no adhesive.

Certain adaptations and modifications of the described embodiments can be made. Therefore, the above discussed embodiments are considered to be illustrative and not restrictive.

The invention claimed is:

1. A system for monitoring a heart condition, the system comprising:
a mobile base unit for positioning on a user and comprising a wireless communication subsystem and a processor;
two or more electrode sensors that are conductively isolated from each other by not having wired interconnections between the two or more electrode sensors, the two or more electrode sensors for wearing on different positions of the user and wirelessly coupled to the base unit, at least one of the electrode sensors for wearing on a peripheral of the user;
a plurality of feedback circuits, each feedback circuit configured to determine localized noise at the respective position on the user of one of the electrode sensors, each feedback circuit configured to insert a voltage signal to the respective position of the user to suppress or cancel the determined noise, each feedback circuit configured to co-ordinate the inserted voltage signal from all of the feedback circuits as a common signal;
wherein the processor is configured to receive a respective signal from the two or more electrode sensors;
wherein the processor is configured to determine heart signal information from the received signals of the two or more electrode sensors, compare the determined heart signal information with expected heart signal information, and transmit a notification based on the comparing,
wherein the base unit is configured to be in communication with a remote monitoring system.

2. The system of claim 1, wherein each of the two or more electrode sensors are configured to be wearable and positionable on different peripherals or a chest of the user.

3. The system of claim 1, further comprising at least one pulse oximetry sensor configured to measure pulse oximetry data.

4. The system of claim 1, wherein the notification based on the comparing is transmitted when a change above a defined threshold is detected by the processor which indicates an abnormal or emergency situation.

5. The system of claim 4, further comprising at least one pulse oximetry sensor configured to measure pulse oximetry data, wherein the threshold comprises a combined threshold of the heart signal information and the pulse oximetry data.

6. The system of claim 4, wherein the transmitting the notification comprises sending the notification according to a defined priority list of remote users.

7. The system of claim 6, wherein the transmitting the notification to the defined priority list of remote users comprises transmitting a first notification to Emergency Medical Services (EMS), transmitting a second notification to a designated family member or plurality of family members, transmitting a third notification to a close neighbour, and transmitting a fourth notification to a patient file for an issuing doctor.

8. The system of claim 7, wherein the first, second, third and fourth notifications are first acknowledged by the user before being sent.

9. The system of claim 6, wherein the defined priority list of remote users comprises at least one of Emergency Medical Services (EMS), a designated family member, a plurality of family members, a close neighbour, or a doctor.

10. The system of claim 1, further comprising a Global Positioning System (GPS) and/or a cell tower triangulation system configured to determine a location of the system.

11. The system of claim 10, further comprising transmitting the location of the system to the remote monitoring system.

12. The system of claim 1, wherein the two or more electrode sensors each include a dry capacitive contact electrode.

13. The system of claim 1, wherein the two or more electrode sensors are configured to be positionable at different positions for determining a differential signal across a heart of the user.

14. The system of claim 1, wherein at least one of the two or more sensors are conductively isolated from the base unit by not having the wired interconnections with the base unit.

15. The system of claim 1, wherein a voltage value of the DC bias signal is commonly known by the at least one of the electrode sensors, the base unit, and/or the another device.

16. The system of claim 1, wherein a voltage value of the DC bias signal is known by the base unit.

17. The system of claim 1, further comprising one or more accelerometers for detecting motion data of the user, wherein the processor is configured to ignore data from at least one of the electrode sensors when motion data of the user exceeds a motion threshold.

18. The system of claim 1, wherein said determining of the heart signal information comprises constructing an electrocardiogram (ECG) signal of a heart of the user.

19. The system of claim 1, wherein the processor is configured to store the received heart signal information from the two or more electrode sensors to a memory.

20. The system of claim 1, wherein the base unit comprises one of the electrode sensors.

21. The system of claim 1, further comprising a hardware system configured to perform the co-ordinating of the inserted voltage signal from all of the feedback circuits as the common signal.

22. The system of claim 1, further comprising a remote device configured to perform the co-ordinating of the inserted voltage signal from all of the feedback circuits as the common signal.

* * * * *